(12) United States Patent
Stearns et al.

(10) Patent No.: US 7,666,584 B2
(45) Date of Patent: Feb. 23, 2010

(54) IDENTIFICATION OF A PIN SPECIFIC GENE AND PROTEIN (PIN-1) USEFUL AS A DIAGNOSTIC TREATMENT FOR PROSTATE CANCER

(75) Inventors: Mark E. Stearns, Villanova, PA (US); Youji Hu, Gulph Mills, PA (US); Min Wang, Gulph Mills, PA (US)

(73) Assignee: Philadelphia Health & Education Coporation, Philadelphia, PA (US)

( * ) Notice: Subject to any disclaimer, the term of this patent is extended or adjusted under 35 U.S.C. 154(b) by 242 days.

(21) Appl. No.: 11/515,475

(22) Filed: Sep. 1, 2006

(65) Prior Publication Data

US 2007/0099214 A1 May 3, 2007

Related U.S. Application Data

(60) Provisional application No. 60/713,284, filed on Sep. 1, 2005.

(51) Int. Cl.
*C12Q 1/00* (2006.01)
*G01N 33/574* (2006.01)

(52) U.S. Cl. .............................. 435/4; 435/7.1; 435/6; 435/7.92; 435/7.23

(58) Field of Classification Search ...................... None
See application file for complete search history.

(56) References Cited

U.S. PATENT DOCUMENTS

| | | | |
|---|---|---|---|
| 4,683,195 | A | 7/1987 | Mullis |
| 4,683,202 | A | 7/1987 | Mullis |
| 4,786,600 | A | 11/1988 | Kramer |
| 4,800,159 | A | 1/1989 | Mullis |
| 4,876,187 | A | 10/1989 | Duck |
| 4,946,778 | A | 8/1990 | Ladner |
| 5,011,769 | A | 4/1991 | Duck |
| 5,023,243 | A | 6/1991 | Tullis |
| 5,132,405 | A | 7/1992 | Huston |
| 5,143,854 | A | 9/1992 | Pirrung |
| 5,412,087 | A | 5/1995 | McGall |
| 5,459,127 | A | 10/1995 | Felgner |
| 5,476,786 | A | 12/1995 | Huston |
| 5,580,859 | A | 12/1996 | Felgner |
| 5,589,466 | A | 12/1996 | Felgner |
| 5,693,622 | A | 12/1997 | Wolff |
| 5,858,719 | A | 1/1999 | Hillman |
| 6,506,559 | B1 | 1/2003 | Fire et al. |
| 2002/0012922 | A1 | 1/2002 | Hilbush et al. |
| 2002/0032319 | A1 | 3/2002 | Cargill et al. |
| 2002/0037508 | A1 | 3/2002 | Cargill et al. |
| 2002/0048766 | A1 | 4/2002 | Doyle et al. |
| 2002/0123107 | A1 | 9/2002 | Chen |
| 2002/0127571 | A1 | 9/2002 | Sutcliffe et al. |
| 2002/0157119 | A1 | 10/2002 | Beachy et al. |
| 2002/0172954 | A1 | 11/2002 | Mao et al. |
| 2003/0039973 | A1 | 2/2003 | Cargill et al. |
| 2003/0044895 | A1 | 3/2003 | Denefle |
| 2003/0092006 | A1 | 5/2003 | Sutcliffe et al. |
| 2003/0224490 | A1 | 12/2003 | Dessain |
| 2004/0166519 | A1 | 8/2004 | Cargill et al. |
| 2004/0178070 | A1 | 9/2004 | Liu |
| 2004/0219539 | A1 | 11/2004 | Millar et al. |
| 2004/0265849 | A1 | 12/2004 | Cargill et al. |
| 2005/0026169 | A1 | 2/2005 | Cargill et al. |
| 2005/0038776 | A1 | 2/2005 | Cyrus et al. |
| 2005/0244834 | A1 | 11/2005 | Lander et al. |
| 2005/0272054 | A1 | 12/2005 | Cargill et al. |
| 2005/0287544 | A1 | 12/2005 | Bertucci et al. |
| 2005/0287559 | A1 | 12/2005 | Cargill et al. |
| 2006/0024700 | A1 | 2/2006 | Cargill et al. |
| 2006/0223093 | A1 | 10/2006 | Luke et al. |
| 2006/0228715 | A1 | 10/2006 | Shiffman et al. |
| 2006/0281082 | A1 | 12/2006 | Zhu |
| 2007/0020633 | A1 | 1/2007 | Millar et al. |
| 2007/0031846 | A1 | 2/2007 | Cargill et al. |
| 2007/0031847 | A1 | 2/2007 | Cargill et al. |
| 2007/0031848 | A1 | 2/2007 | Cargill et al. |
| 2007/0037196 | A1 | 2/2007 | Gibson et al. |
| 2007/0042382 | A1 | 2/2007 | Cargill et al. |
| 2007/0054278 | A1 | 3/2007 | Cargill |
| 2007/0059710 | A1 | 3/2007 | Luke et al. |
| 2007/0122826 | A1 | 5/2007 | Glass et al. |

FOREIGN PATENT DOCUMENTS

| | | |
|---|---|---|
| WO | WO 89/12690 | 12/1989 |
| WO | WO 90/15070 | 12/1990 |
| WO | WO 92/10092 | 6/1992 |
| WO | WO 95/11995 | 5/1995 |
| WO | WO 95/18863 | 7/1995 |
| WO | WO 95/21931 | 8/1995 |
| WO | WO 96/17823 | 6/1996 |
| WO | WO 96/25508 | 8/1996 |

OTHER PUBLICATIONS

Petry et al. BBRC, vol. 300, p. 343-350, 2003.*

(Continued)

*Primary Examiner*—Larry R. Helms
*Assistant Examiner*—Lei Yao
(74) *Attorney, Agent, or Firm*—Drinker Biddle & Reath LLP

(57) ABSTRACT

The invention relates to nucleic acids encoding a mammalian ABCA5 gene, and proteins encoded thereby, whose expression is increased in certain diseases, disorders, or conditions, including, but not limited to, PIN. Further, the invention relates to diagnostic assays for identifying the DNA-binding protein ABCA5 (also known as PIN-1). The invention also relates to oligonucleotide sequence(s) or antibodies that specifically bind with ABCA5 or variants thereof.

5 Claims, 8 Drawing Sheets

OTHER PUBLICATIONS

Petry et al. in Biochem. J. vol. 393, p. 79-87, 2006.*

Hu et al Clin. Cancer, vol. 13, p. 929-938, 2007.*

Arakawa et al., "High Grade Prostatic Intraepithelial Neoplasia in Prostates Removed Following Irradiation Failure in the Treatment of Prostatic Carcinoma," *Pathol. Res. Pract.*, vol. 191, pp. 868-872, 1995.

Bishara et al, "High-Grade Prostatic Intraepithelial Neoplasia on Needle Biopsy: Risk of Cancer on Repeat Biopsy Related to Number of Involved Cores and Morphologic Pattern," *Am J Surg Pathol.*, vol. 28, pp. 629-633, 2004.

Bostwick et al. "Atypical Adenomatous Hyperplasia of the Prostate: Relationship With Carcinoma in 217 Whole Mount Radical Prostatectomies," *Am J Surg Pathol*, vol. 19, pp. 506-518, 1995.

Bostwick et al, "Prostatic Intraepithelial Neoplasia. and Early Invasion in Prostate Cancer," *Cancer*, vol. 59, pp. 788-794, 1987.

Bostwick et al, "High Grade Prostatic Intraepithelial Neoplasia: The Most Likely Precursor of Prostate Cancer," *Cancer*, vol. 75, pp. 1823-1836,1995.

Bradford, M.M. et al., "A Rapid and Sensitive Method for the Quantitation of Microgram Quantities of Protein Utilizing the Principles of Protein-Dye Binding," *Anal. Biochem.*, vol. 72, pp. 248-254, 1976.

Brawer, M.K. et al., "Significance of Prostatic Intraepithelial Neoplasia on Prostate Needle Biopsy," *Urology*, vol. 38, pp. 103-107, 1991.

Davidson, D et al, "Prostatic Intraepithelial Neoplasia is a Risk Factor for Adenocarcinoma Predictive Accuracy in Needle Biopsies," *J. Urol.*, vol. 154, pp. 1295-1299, 1995.

Dean, M. et al., "The Human ATP-Binding Cassette (ABC) Transporter Superfamily," *J Lipid Res.*, vol. 42, pp. 1007-1017, 2001.

Dean, M., et al., "The Human ATP-Binding Cassette (ABC) Transporter Superfamily," *Genome Res.*, vol, 11, pp. 1156-1166, 2001.

Epstein, J.I. et al., "Relationship of Severe Dysplasia to Stage a (Incidental) Adenocarcinoma of the Prostate," *Cancer*, vol. 65, pp, 2321-2327, 1990.

Frangioni, J.V et al., "Solubilization and Purification of Enzymatically Active Glutathione S-Transferase (Pgex) Fusion Proteins," *Analytical Biochemistry*, vol. 210, pp. 179-187, 1993.

Gokden, N., et al., "High-Grade Prostatic Intraepithelial Neoplasia in Needle Biopsy as Risk Factor for Detection of Adenocarcinoma: Current Level of Risk in Screening Population," *Am Journal Surg Pathol.*, vol. 28(5), pp. 629-633, 2004.

Haggman, M.J. et al., The Relationship Between Prostatic Intraepithelial Neoplasia and Prostate Cancer: Critical Issues. *Journal of Urology*, vol. 158, pp. 12-22, 1997.

Kovi, J., et al., "Large Acinar Atypical Hyperplasia and Carcinoma of the Prostate," *Cancer*, vol. 61, pp. 555-561, 1988.

Langmann, T., et al., "Real-Time Reverse Transcription-PCR Expression Profiling of the Complete Human ATP-Binding Cassette Transporter Superfamily in Various Tissues," *Clinical Chemistry*, vol. 49, pp. 230-238, 2003.

Ohkia, A., et al., "Evidence for a Prostate Cancer Associated Diagnostic Marker-1, PCADM-1: immunohistochemistry and In Situ Hybridization Studies," *Clin. Can. Res.*, vol. 10; pp. 2452-2458, 2004.

Orozco, R et al., "Observations on Pathology Trends in 62,537 Prostate Biopsies Obtained From Urology Private Practices in the United States, " *Urology*, vol. 51 pp. 186-195, 1998.

Petry, F, et al., "Subcellular Localization of Rabca5, a Rat ATP-Binding Cassette Transporter Expressed in Leydig Cells, and Characterization of its Splice Variant Apparently Encoding a Halftransporter," *Biochem Journal*, vol. 393, pp. 79-87, 2006.

Petry, F., et al., "Cloning of Human and Rat ABCA5/Abca5 and Detection of a Human Splice Variant," *Biochem. Biophys.Res. Commun.*, vol. 300, pp. 343-350. 2003.

Qian, J et al., "The Extent and Multicentricity of High-Grade Prostatic Intraepithelial Neoplasia in Clinically Localized Prostatic Adenocarcinoma," *Hum. Pathol*, vol. 28, pp. 143-148, 1997.

Sakr, W.A., "Prostatic Intraepithelial Neoplasia: A Marker for High-Risk Groups and a Potential Target for Chemoprevention," *Eur. Urol*, vol. 35, pp. 474-478, 1999.

Sakr, W.A et al., "High Grade Prostatic Intraepithelial Neoplasia (HGPIN) and Prostatic Adenocarcinoma Between the Ages of 20-69: An Autopsy Study of 249 Cases," In Vivo, vol, 8, pp. 439-443, 1994.

Singh, H., et al., "Molecular Cloning of an Enhancer Binding Protein: Isolation by Screening of an Expression Library With a Recognition Site DNA," *Cell*, vol. 52, pp. 415-423, 1988.

Stearns, M.E et al., "Immunoassays of the Metalloproteinase (MMP-2) and Tissue Inhibitor of Metalloproteinase (TIMP-1, 2) Levels in Non-Invasive and Metastatic PC-3 Clones Effects of Taxol," *Oncol. Res.*, vol. 6, pp. 195-201, 1994.

Towbin, H et al., "Electrophoretic Transfer of Proteins from Polyacrylamide Gels to Nitrocellulose Sheets; Procedures and Some Applications," *Proc. Natl. Acad. Sci. U.S.A.*, vol. 76, pp. 4350-4354, 1979.

Weinstein, M.H et al., "Significance of High Grade Prostatic Intraepithelial Neoplasia on Needle Biopsy," *Human Pathol.*, vol. 24, pp. 624-629, 1993.

\* cited by examiner

Figure 1

GAATTCAGAAAAGAAAAAAAGATTTGCTATTTCTACATTCTCCCTGAGCATTAAG
ACTTCCCTTGCCCATTCCTCAATTCAAAGCTAAGGCTTCTTCTGGAGCTGCCTCTG
TGGGCGGTTCGGGAGATACCAAAGGAGAAAAAGTACCACTGTTGATATGGTGGT
ATTTCAAATTCTGGTCTACCCTATTTCACATGCCTTGTTTACTTTTCAGAGCTGAC
AGATTGCTGCTCCATGCATTCTGTCCAGTTTCCTAAGAGAGACAGCTTGGAGTAT
GCTTAATCCATCTTACCTGGGACTGAAACAGCTGCTTATTTTGCCGTTAAAAATT
ACATGCAGTTTACTGCGTGGCTCCGGGTTTGTTTGTTTGTTTTCCTCTTTAATAG
GTTTATTCAGAAAACATGTCCACTGCAATTAGGGAGGTAGGAGTTTGGAGACAG
ACCAGAACACTTCTACTGAAGAATTACTTAATTAAATGCAGAACCAAAAAGAGT
AGTGTTCAGGAAATTCTTTTTCCACTATTTTTTTATTTTGGTTAATATTAATTAGC
ATGATGCATCCAAATAAGAAATATGAAGAAGTGCCTAATATAGAACTCAATCCT
ATGGACAAGTTTACTCTTTCTAATCTAATTCTTGGATATACTCCAGTGACTAATAT
TACAAGCAGCATCATGCAGAAAGTGTCTACTGATCATCTACCTGATGTCATAATT
ACTGAAGAATATACAAATGAAAAGAAATGTTAACATCCAGTCTCTCTAAGCCG
AGCAACTTTGTAGGTGTGGTTTTCAAAGACTCCATGTCCTATGAACTTCGTTTTTT
TCCTGATATGATTCCAGTATCTTCTATTTATATGGATTCAAGAGCTGGCTGTTCAA
AATCATGTGAGGCTGCTCAGTACTGGTCCTCAGGTTTCACAGTTTTACAAGCATC
CATAGATGCTGCCATTATACAGTTGAAGACCAATGTTTCTCTTGGAAGGAGCTG
GAGTCAACTAAAGCTGTTATTATGGGAGAAACTGCTGTTGTAGAAATAGATACCT
TTCCCCGAGGAGTAATTTTAATATACCTAGTTATAGCATTTTCACCTTTTGGATAC
TTTTTGGCAATTCATATCGTAGCAGAAAAAGAAAAAAAAATAAAAGAATTTTTA
AAGATAATGGGACTTCATGATACTGCCTTTTGGCTTTCCTGGGTTCTTCTATATAC
AAGTTTAATTTTTCTTATGTCCCTTCTTATGGCAGTCATTGCGACAGCTTCTTTGTT
ATTTCCTCAAAGTAGCAGCATTGTGATATTCTGCTTTTTTCCTTTATGGATTAT
CATCTGTATTTTTGCTTTAATGCTGACACCTCTTTTAAAAAATCAAACATGTG
GGAATAGTTGAATTTTTTGTTACTGTGGCTTTTGGATTTATTGGCCTTATGATAAT
CCTCATAGAAAGTTTTCCCAAATCGTTAGTGTGGCTTTTCAGTCCTTTCTGTCACT
GTACTTTTGTGATTGGTATTGCACAGGTCATGCATTTAGAAGATTTTAATGAAGG
TGCTTCATTTTCAAATTTGACTGCAGGCCCATATCCTCTAATTATTACAATTATCA
TGCTCACACTTAATAGTATATTCTATGTCCTCTTGGCTGTCTATCTTGATCAAGTC
ATTCCAGGGGAATTTGGCTTACGGAGATCATCTTTATATTTTCTGAAGCCTTCATA
TTGGTCAAAGAGCAAAAGAAATTATGAGGAGTTATCAGAGGGCAATGTTAATGG
AAATATTAGTTTTAGTGAAATTATTGAGCCAGTTTCTTCAGAATTTGTAGGAAAA
GAAGCCATAAGAATTAGTGGTATTCAGAAGACATACAGAAAGAAGGGTGAAAA
TGTGGAGGCTTTGAGAAATTTGTCATTTGACATATATGAGGGTCAGATTACTGCC
TTACTTGGCCACAGTGGAACAGGAAAGAGTACATTGATGAATATTCTTTGTGGAC
TCTGCCCACCTTCTGATGGGTTTGCATCTATATATGGACACAGAGTCTCAGAAAT
AGATGAAATGTTTGAAGCAAGAAAAATGATTGGCATTTGTCCACAGTTAGATAT
ACACTTTGATGTTTTGACAGTAGAAGAAATTTATCAATTTTGGCTTCAATCAAA
GGGATACCAGCCAACAATATAATACAAGAAGTGCAGAAGGTTTTACTAGATTTA
GACATGCAGACTATCAAAGATAACCAAGCTAAAAAATTAAGTGGTGGTCAAAAA
AGAAAGCTGTCATTAGGAATTGCTGTTCTTGGGAACCCAAAGATACTGCTGCTAG
ATGAACCAACAGCTGGAATGGACCCCTGTTCTCGACATATTGTATGGAATCTTTT
AAAATACAGAAAGCCAATCGGGTGACAGTGTTCAGTACTCATTTCATGGATGA
AGCTGACATTCTTGCAGATAGGAAAGCTGTGATATCACAAGGAATGCTGAAATG

Figure 1 (cont.)

TGTTGGTTCTTCAATGTTCCTCAAAAGTAAATGGGGGATCGGCTACCGCCTGAGC
ATGTACATAGACAAATATTGTGCCACAGAATCTCTTTCTTCACTGGTTAAACAAC
ATATACCTGGAGCTACTTTATTACAACAGAATGACCAACAACTTGTGTATAGCTT
GCCTTTCAAGGACATGGACAAATTTTCAGGTTTGTTTCTGCCCTAGACAGTCATT
CAAATTTGGGTGTCATTTCTTATGGTGTTTCCATGACGACTTTGGAAGACGTATTT
TTAAAGCTAGAAGTTGAAGCAGAAATTGACCAAGCAGATTATAGTGTATTTACTC
AGCAGCCACTGGAGGAAGAAATGGATTCAAAATCTTTTGATGAAATGGAACAGA
GCTTACTTATTCTTTCTGAAACCAAGGCTGCTCTAGTGAGCACCATGAGCCTTTG
GAAACAACAGATGTATACAATAGCAAAGTTTCATTTCTTTACCTTGAAACGTGAA
AGTAAATCAGTGAGATCAGTGTTGCTTCTGCTTTTAATTTTTTTCACAGTTCAGAT
TTTTATGTTTTTGGTTCATCACTCTTTTAAAAATGCTGTGGTTCCCATCAAACTTG
TTCCAGACTTATATTTTCTAAAACCTGGAGACAAACCACATAAATACAAAACAA
GTCTGCTTCTTCAAAATTCTGCTGACTCAGATATCAGTGATCTTATTAGCTTTTTC
ACAAGCCAGAACATAATGGTGACGATGATTAATGACAGTGACTATGTATCCGTG
GCTCCCCATAGTGCGGCTTTAAATGTGATGCATTCAGAAAAGGACTATGTTTTG
CAG
(SEQ ID NO:1)

Figure 2

MSTAIREVGVWRQTRTLLLKNYLIKCRTKKSSVQEILFPLFFLFWLILISMMHPNKKY
EEVPNIELNPMDKFTLSNLILGYTPVTNITSSIMQKVSTDHLPDVIITEEYTNEKEMLTS
SLSKPSNFVGVVFKDSMSYELRFFPDMIPVSSIYMDSRAGCSKSCEAAQYWSSGFTV
LQASIDAAIIQLKTNVSLWKELESTKAVIMGETAVVEIDTFPRGVILIYLVIAFSPFGYF
LAIHIVAEKEKKIKEFLKIMGLHDTAFWLSWVLLYTSLIFLMSLLMAVIATASLLFPQS
SSIVIFLLFFLYGLSSVFFALMLTPLFKKSKHVGIVEFFVTVAFGFIGLMIILIESFPKSLV
WLFSPFCHCTFVIGIAQVMHLEDFNEGASFSNLTAGPYPLIITIIMLTLNSIFYVLLAVY
LDQVIPGEFGLRRSSLYFLKPSYWSKSKRNYEELSEGNVNGNISFSEIIEPVSSEFVGKE
AIRISGIQKTYRKKGENVEALRNLSFDIYEGQITALLGHSGTGKSTLMNILCGLCPPSD
GFASIYGHRVSEIDEMFEARKMIGICPQLDIHFDVLTVEENLSILASIKGIPANNIIQEV
QKVLLDLDMQTIKDNQAKKLSGGQKRKLSLGIAVLGNPKILLLDEPTAGMDPCSRHI
VWNLLKYRKANRVTVFSTHFMDEADILADRKAVISQGMLKCVGSSMFLKSKWGIG
YRLSMYIDKYCATESLSSLVKQHIPGATLLQQNDQQLVYSLPFKDMDKFSGLFSALD
SHSNLGVISYGVSMTTLEDVFLKLEVEAEIDQADYSVFTQQPLEEEMDSKSFDEMEQ
SLLILSETKAALVSTMSLWKQQMYTIAKFHFFTLKRESKSVRSVLLLLIFFTVQIFMF
LVHHSFKNAVVPIKLVPDLYFLKPGDKPHKYKTSLLLQNSADSDISDLISFFTSQNIM
VTMINDSDYVSVAPHSAALNVMHSEKDYVFA (SEQ ID NO:2)

Figure 7

| Tissue | Urine |
|---|---|
| PIN (n=11/11) | PIN (n=10/10) |
| SV (n=0/11) | PIN/PCA (n=8/8) |
| Stroma (n=0/11) | PCA (0/4) |
| BPH (0/11) | BPH (0/10) |
| PCA (n=0/11) | |

*Note that only the PIN tissue and urine of PIN patients or patients with PIN and PCA expressed ABCA5. The PIN urines were strongly positive and the PIN/PCA urine specimens were faintly positive

Figure 8

TCCAGCGA (SEQ ID NO:3)

Figure 11
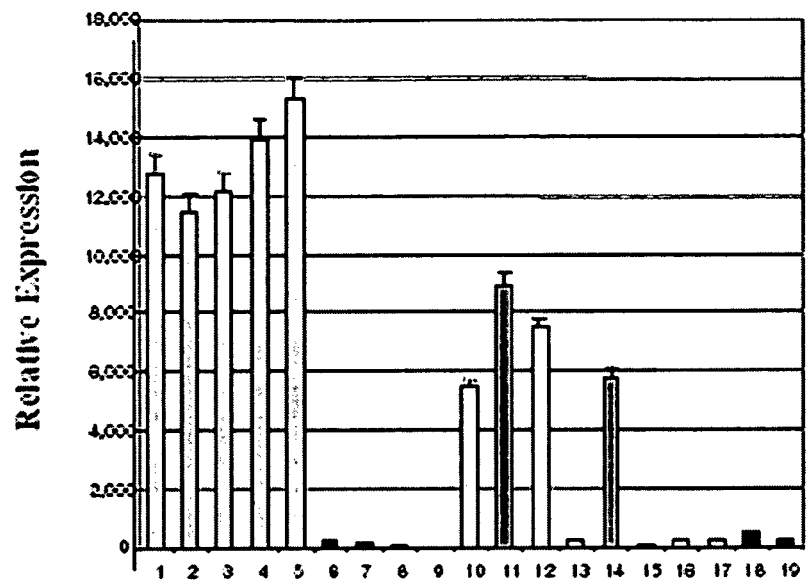
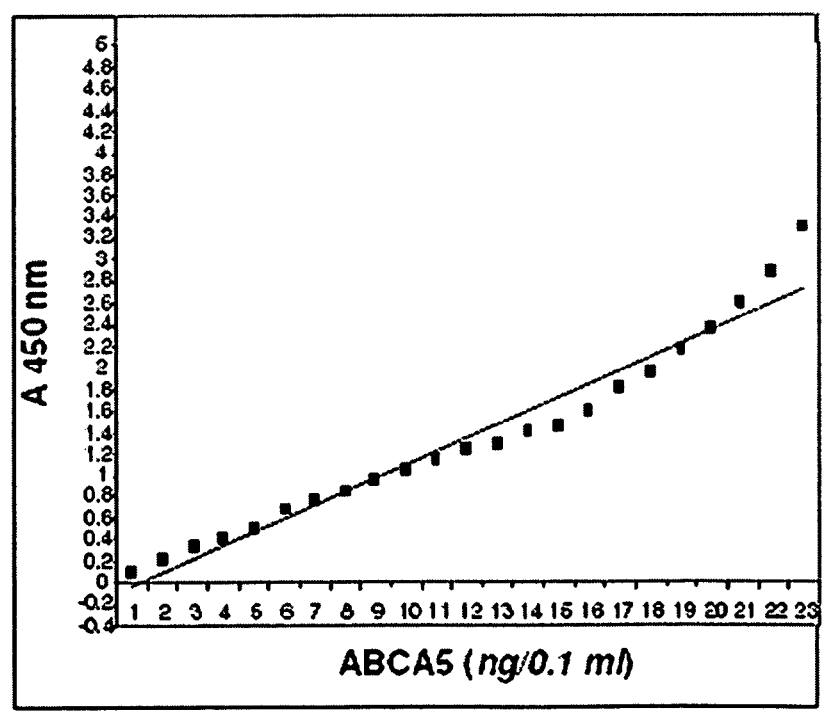
Figure 12

Figure 13a
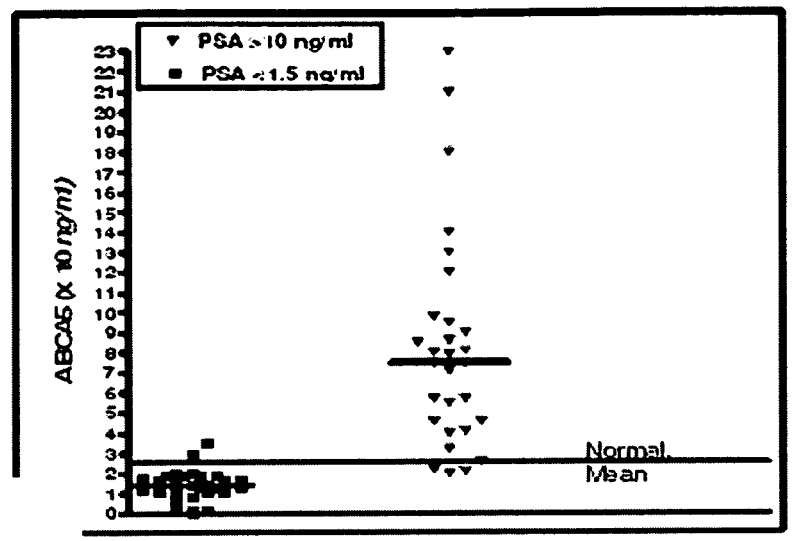
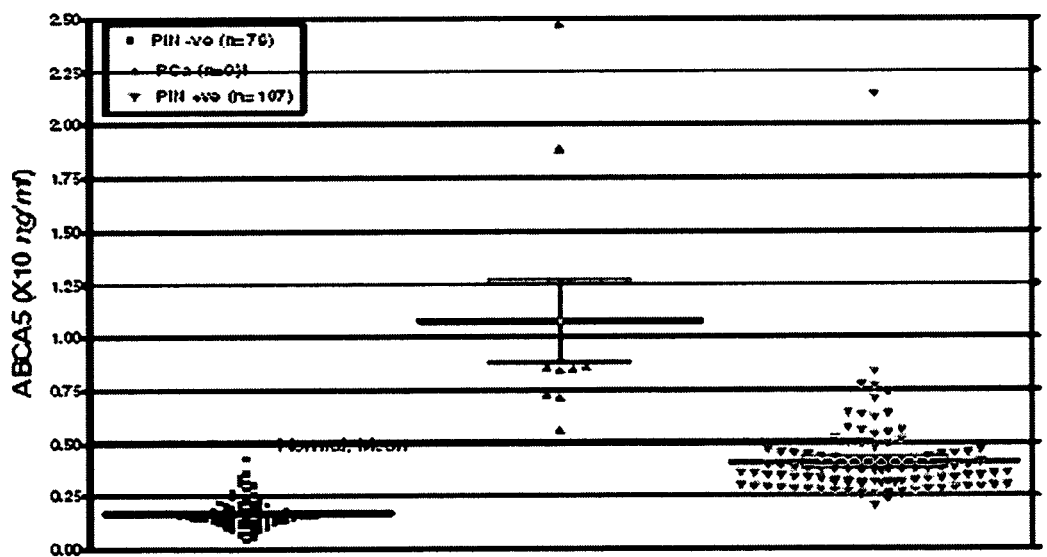
Figure 13b

SEQUENCE LISTING

<160> NUMBER OF SEQ ID NOS: 9

<210> SEQ ID NO 1
<211> LENGTH: 3310
<212> TYPE: DNA
<213> ORGANISM: homo sapiens

<400> SEQUENCE: 1

```
gaattcagaa aagaaaaaaa gatttgctat ttctacattc tccctgagca ttaagacttc    60
ccttgcccat tcctcaattc aaagctaagg cttcttctgg agctgcctct gtgggcggtt   120
cgggagatac caaggagaa aaagtaccac tgttgatatg gtggtatttc aaattctggt    180
ctaccctatt tcacatgcct tgtttacttt tcagagctga cagattgctg ctccatgcat   240
tctgtccagt ttcctaagag agacagcttg gagtatgctt aatccatctt acctgggact   300
gaaacagctg cttattttgc cgttaaaaat tacatgcagt ttactgcgtg gctccgggtt   360
tgtttgtttg ttttcctct taataggtt tattcagaaa acatgtccac tgcaattagg     420
gaggtaggag tttggagaca gaccagaaca cttctactga agaattactt aattaaatgc   480
agaaccaaaa agagtagtgt tcaggaaatt ctttttccac tatttttttt attttggtta   540
atattaatta gcatgatgca tccaaataag aaatatgaag aagtgcctaa tatagaactc   600
aatcctatgg acaagtttac tctttctaat ctaattcttg gatatactcc agtgactaat   660
attacaagca gcatcatgca gaaagtgtct actgatcatc tacctgatgt cataattact   720
gaagaatata caaatgaaaa agaaatgtta acatccagtc tctctaagcc gagcaacttt   780
gtaggtgtgg ttttcaaaga ctccatgtcc tatgaacttc gttttttttcc tgatatgatt   840 ccagtatctt ctatttatat ggattcaaga gctggctgtt caaaatcatg tgaggctgct   900
cagtactggt cctcaggttt cacagtttta caagcatcca tagatgctgc cattatacag   960
ttgaagacca atgtttctct ttggaaggag ctggagtcaa ctaaagctgt tattatggga  1020
gaaactgctg ttgtagaaat agatacccttt ccccgaggag taattttaat atacctagtt 1080
atagcatttt cacctttttgg atacttttgt gcaattcata tcgtagcaga aaaagaaaaa 1140
aaaataaaag aattttaaaa gataatggga cttcatgata ctgccttttg gctttcctgg  1200
gttcttctat atacaagttt aatttttctt atgtcccttc ttatggcagt cattgcgaca  1260
gcttctttgt tatttcctca aagtagcagc attgtgatat ttctgctttt tttcctttat  1320
ggattatcat ctgtattttt tgctttaatg ctgacacctc ttttaaaaa atcaaaacat   1380 gtgggaatag ttgaattttt tgttactgtg gcttttggat ttattggcct tatgataatc   1440
ctcatagaaa gttttcccaa atcgttagtg tggcttttca gtcctttctg tcactgtact  1500
tttgtgattg gtattgcaca ggtcatgcat ttagaagatt ttaatgaagg tgcttcattt  1560
tcaaatttga ctgcaggccc atatcctcta attattacaa ttatcatgct cacacttaat  1620
agtatattct atgtcctctt ggctgtctat cttgatcaag tcattccagg ggaatttggc  1680
ttacggagat catctttata ttttctgaag ccttcatatt ggtcaaagag caaagaaat   1740 tatgaggagt tatcagaggg caatgttaat ggaaatatta gttttagtga aattattgag  1800
ccagtttctt cagaatttgt aggaaaagaa gccataagaa ttagtggtat tcagaagaca  1860
tacagaaaga agggtgaaaa tgtggaggct ttgagaaatt tgtcatttga catatatgag  1920
ggtcagatta ctgccttact tggccacagt ggaacaggaa agagtacatt gatgaatatt  1980
ctttgtggac tctgcccacc ttctgatggg tttgcatcta tatatggaca cagagtctca  2040
gaaatagatg aaatgtttga agcaagaaaa atgattggca tttgtccaca gttagatata  2100
cactttgatg tttttgacagt agaagaaaat ttatcaattt tggcttcaat caaagggata  2160
ccagccaaca atataataca agaagtgcag aaggttttac tagatttaga catgcagact  2220
atcaaagata accaagctaa aaaattaagt ggtggtcaaa aagaaagct gtcattagga    2280 attgctgttc ttgggaaccc aaagatactg ctgctagatg aaccaacagc tggaatggac  2340
ccctgttctc gacatattgt atggaatctt ttaaaatca gaaaagccaa tcgggtgaca   2400
```

```
gtgttcagta ctcatttcat ggatgaagct gacattcttg cagataggaa agctgtgata    2460
tcacaaggaa tgctgaaatg tgttggttct tcaatgttcc tcaaaagtaa atggggatc     2520 ggctaccgcc tgagcatgta catagacaaa tattgtgcca cagaatctct ttcttcactg    2580
gttaaacaac atatacctgg agctacttta ttacaacaga atgaccaaca acttgtgtat    2640
agcttgcctt tcaaggacat ggacaaattt tcaggtttgt tttctgccct agacagtcat    2700
tcaaatttgg gtgtcatttc ttatggtgtt tccatgacga ctttggaaga cgtatttta    2760 aagctagaag ttgaagcaga aattgaccaa gcagattata gtgtatttac tcagcagcca    2820
ctggaggaag aaatggattc aaaatctttt gatgaaatgg aacagagctt acttattctt    2880
tctgaaacca aggctgctct agtgagcacc atgagccttt ggaaacaaca gatgtataca    2940
atagcaaagt ttcatttctt taccttgaaa cgtgaaagta aatcagtgag atcagtgttg    3000
cttctgcttt taattttttt cacagttcag attttttatgt ttttggttca tcactctttt    3060
aaaaatgctg tggttcccat caaacttgtt ccagactat attttctaaa acctggagac     3120
aaaccacata atacaaaac aagtctgctt cttcaaaatt ctgctgactc agatatcagt     3180
gatcttatta gcttttttcac aagccagaac ataatggtga cgatgattaa tgacagtgac   3240
tatgtatccg tggctcccca tagtgcggct ttaaatgtga tgcattcaga aaaggactat    3300
gtttttgcag                                                          3310

<210> SEQ ID NO 2
<211> LENGTH: 969
<212> TYPE: PRT
<213> ORGANISM: Homo sapiens

<400> SEQUENCE: 2

Met Ser Thr Ala Ile Arg Glu Val Gly Val Trp Arg Gln Thr Arg Thr
1               5                   10                  15

Leu Leu Leu Lys Asn Tyr Leu Ile Lys Cys Arg Thr Lys Lys Ser Ser
            20                  25                  30

Val Gln Glu Ile Leu Phe Pro Leu Phe Phe Leu Phe Trp Leu Ile Leu
        35                  40                  45

Ile Ser Met Met His Pro Asn Lys Lys Tyr Glu Glu Val Pro Asn Ile
    50                  55                  60

Glu Leu Asn Pro Met Asp Lys Phe Thr Leu Ser Asn Leu Ile Leu Gly
65                  70                  75                  80

Tyr Thr Pro Val Thr Asn Ile Thr Ser Ile Met Gln Lys Val Ser
                85                  90                  95

Thr Asp His Leu Pro Asp Val Ile Ile Thr Glu Glu Tyr Thr Asn Glu
            100                 105                 110

Lys Glu Met Leu Thr Ser Ser Leu Ser Lys Pro Ser Asn Phe Val Gly
        115                 120                 125

Val Val Phe Lys Asp Ser Met Ser Tyr Glu Leu Arg Phe Phe Pro Asp
    130                 135                 140

Met Ile Pro Val Ser Ser Ile Tyr Met Asp Ser Arg Ala Gly Cys Ser
145                 150                 155                 160

Lys Ser Cys Glu Ala Ala Gln Tyr Trp Ser Ser Gly Phe Thr Val Leu
                165                 170                 175

Gln Ala Ser Ile Asp Ala Ala Ile Ile Gln Leu Lys Thr Asn Val Ser
            180                 185                 190

Leu Trp Lys Glu Leu Glu Ser Thr Lys Ala Val Ile Met Gly Glu Thr
        195                 200                 205
```

```
Ala Val Val Glu Ile Asp Thr Phe Pro Arg Gly Val Ile Leu Ile Tyr
    210                 215                 220

Leu Val Ile Ala Phe Ser Pro Phe Gly Tyr Phe Leu Ala Ile His Ile
225                 230                 235                 240

Val Ala Glu Lys Glu Lys Lys Ile Lys Glu Phe Leu Lys Ile Met Gly
                245                 250                 255

Leu His Asp Thr Ala Phe Trp Leu Ser Trp Val Leu Leu Tyr Thr Ser
                260                 265                 270

Leu Ile Phe Leu Met Ser Leu Leu Met Ala Val Ile Ala Thr Ala Ser
            275                 280                 285

Leu Leu Phe Pro Gln Ser Ser Ser Ile Val Ile Phe Leu Leu Phe Phe
            290                 295                 300

Leu Tyr Gly Leu Ser Ser Val Phe Phe Ala Leu Met Leu Thr Pro Leu
305                 310                 315                 320

Phe Lys Lys Ser Lys His Val Gly Ile Val Glu Phe Phe Val Thr Val
                325                 330                 335

Ala Phe Gly Phe Ile Gly Leu Met Ile Ile Leu Ile Glu Ser Phe Pro
                340                 345                 350

Lys Ser Leu Val Trp Leu Phe Ser Pro Phe Cys His Cys Thr Phe Val
            355                 360                 365

Ile Gly Ile Ala Gln Val Met His Leu Glu Asp Phe Asn Glu Gly Ala
370                 375                 380

Ser Phe Ser Asn Leu Thr Ala Gly Pro Tyr Pro Leu Ile Ile Thr Ile
385                 390                 395                 400

Ile Met Leu Thr Leu Asn Ser Ile Phe Tyr Val Leu Leu Ala Val Tyr
                405                 410                 415

Leu Asp Gln Val Ile Pro Gly Glu Phe Gly Leu Arg Arg Ser Ser Leu
                420                 425                 430

Tyr Phe Leu Lys Pro Ser Tyr Trp Ser Lys Ser Lys Arg Asn Tyr Glu
            435                 440                 445

Glu Leu Ser Glu Gly Asn Val Asn Gly Asn Ile Ser Phe Ser Glu Ile
450                 455                 460

Ile Glu Pro Val Ser Ser Glu Phe Val Gly Lys Glu Ala Ile Arg Ile
465                 470                 475                 480

Ser Gly Ile Gln Lys Thr Tyr Arg Lys Lys Gly Glu Asn Val Glu Ala
                485                 490                 495

Leu Arg Asn Leu Ser Phe Asp Ile Tyr Glu Gly Gln Ile Thr Ala Leu
                500                 505                 510

Leu Gly His Ser Gly Thr Gly Lys Ser Thr Leu Met Asn Ile Leu Cys
            515                 520                 525

Gly Leu Cys Pro Pro Ser Asp Gly Phe Ala Ser Ile Tyr Gly His Arg
            530                 535                 540

Val Ser Glu Ile Asp Glu Met Phe Glu Ala Arg Lys Met Ile Gly Ile
545                 550                 555                 560

Cys Pro Gln Leu Asp Ile His Phe Asp Val Leu Thr Val Glu Glu Asn
                565                 570                 575

Leu Ser Ile Leu Ala Ser Ile Lys Gly Ile Pro Ala Asn Asn Ile Ile
                580                 585                 590

Gln Glu Val Gln Lys Val Leu Leu Asp Leu Asp Met Gln Thr Ile Lys
            595                 600                 605

Asp Asn Gln Ala Lys Lys Leu Ser Gly Gly Gln Lys Arg Lys Leu Ser
610                 615                 620
```

```
Leu Gly Ile Ala Val Leu Gly Asn Pro Lys Ile Leu Leu Asp Glu
625                 630                 635                 640

Pro Thr Ala Gly Met Asp Pro Cys Ser Arg His Ile Val Trp Asn Leu
            645                 650                 655

Leu Lys Tyr Arg Lys Ala Asn Arg Val Thr Val Phe Ser Thr His Phe
            660                 665                 670

Met Asp Glu Ala Asp Ile Leu Ala Asp Arg Lys Ala Val Ile Ser Gln
            675                 680                 685

Gly Met Leu Lys Cys Val Gly Ser Ser Met Phe Leu Lys Ser Lys Trp
            690                 695                 700

Gly Ile Gly Tyr Arg Leu Ser Met Tyr Ile Asp Lys Tyr Cys Ala Thr
705                 710                 715                 720

Glu Ser Leu Ser Ser Leu Val Lys Gln His Ile Pro Gly Ala Thr Leu
            725                 730                 735

Leu Gln Gln Asn Asp Gln Gln Leu Val Tyr Ser Leu Pro Phe Lys Asp
            740                 745                 750

Met Asp Lys Phe Ser Gly Leu Phe Ser Ala Leu Asp Ser His Ser Asn
            755                 760                 765

Leu Gly Val Ile Ser Tyr Gly Val Ser Met Thr Thr Leu Glu Asp Val
770                 775                 780

Phe Leu Lys Leu Glu Val Glu Ala Glu Ile Asp Gln Ala Asp Tyr Ser
785                 790                 795                 800

Val Phe Thr Gln Gln Pro Leu Glu Glu Met Asp Ser Lys Ser Phe
            805                 810                 815

Asp Glu Met Glu Gln Ser Leu Leu Ile Leu Ser Glu Thr Lys Ala Ala
            820                 825                 830

Leu Val Ser Thr Met Ser Leu Trp Lys Gln Gln Met Tyr Thr Ile Ala
            835                 840                 845

Lys Phe His Phe Phe Thr Leu Lys Arg Glu Ser Lys Ser Val Arg Ser
            850                 855                 860

Val Leu Leu Leu Leu Ile Phe Phe Thr Val Gln Ile Phe Met Phe
865                 870                 875                 880

Leu Val His His Ser Phe Lys Asn Ala Val Pro Ile Lys Leu Val
            885                 890                 895

Pro Asp Leu Tyr Phe Leu Lys Pro Gly Asp Lys Pro His Lys Tyr Lys
            900                 905                 910

Thr Ser Leu Leu Leu Gln Asn Ser Ala Asp Ser Ile Ser Asp Leu
            915                 920                 925

Ile Ser Phe Phe Thr Ser Gln Asn Ile Met Val Thr Met Ile Asn Asp
            930                 935                 940

Ser Asp Tyr Val Ser Val Ala Pro His Ser Ala Ala Leu Asn Val Met
945                 950                 955                 960

His Ser Glu Lys Asp Tyr Val Phe Ala
            965

<210> SEQ ID NO 3
<211> LENGTH: 8
<212> TYPE: DNA
<213> ORGANISM: Artificial
<220> FEATURE:
<223> OTHER INFORMATION: DNA probe

<400> SEQUENCE: 3 tccagcga                                                          8
```

```
<210> SEQ ID NO 4
<211> LENGTH: 26
<212> TYPE: DNA
<213> ORGANISM: artificial
<220> FEATURE:
<223> OTHER INFORMATION: forward primer

<400> SEQUENCE: 4
ggctgctatt ctgaccactc actata                                    26

<210> SEQ ID NO 5
<211> LENGTH: 22
<212> TYPE: DNA
<213> ORGANISM: artificial
<220> FEATURE:
<223> OTHER INFORMATION: reverse primer

<400> SEQUENCE: 5
ttaactgccc agacaccatg at                                        22

<210> SEQ ID NO 6
<211> LENGTH: 20
<212> TYPE: DNA
<213> ORGANISM: artificial
<220> FEATURE:
<223> OTHER INFORMATION: forward primer

<400> SEQUENCE: 6
tgttaccaac tgggacgaca                                           20

<210> SEQ ID NO 7
<211> LENGTH: 21
<212> TYPE: DNA
<213> ORGANISM: artificial
<220> FEATURE:
<223> OTHER INFORMATION: reverse primer

<400> SEQUENCE: 7
aaggaaggct ggaaaaagag c                                         21

<210> SEQ ID NO 8
<211> LENGTH: 22
<212> TYPE: PRT
<213> ORGANISM: homo sapiens

<400> SEQUENCE: 8

Met Ser Thr Ala Ile Arg Glu Val Gly Val Trp Arg Gln Thr Arg Thr
1               5                   10                  15

Leu Leu Leu Lys Asn Tyr
            20

<210> SEQ ID NO 9
<211> LENGTH: 22
<212> TYPE: PRT
<213> ORGANISM: homo sapiens

<400> SEQUENCE: 9

Phe Ser Gly Leu Phe Ser Ala Leu Asp Ser His Ser Asn Leu Gly Val
1               5                   10                  15

Ile Ser Tyr Gly Val Ser
            20
```

IDENTIFICATION OF A PIN SPECIFIC GENE AND PROTEIN (PIN-1) USEFUL AS A DIAGNOSTIC TREATMENT FOR PROSTATE CANCER

CROSS-REFERENCE TO RELATED APPLICATIONS

This application is entitled to priority under 35 U.S.C. § 119(e), to U.S. Provisional Application No. 60/713,284, filed on Sep. 1, 2005, which application is hereby incorporated herein by reference in its entirety.

STATEMENT REGARDING FEDERALLY SPONSORED STATEMENT REGARDING FEDERALLY SPONSORED RESEARCH OR DEVELOPMENT

This invention was supported in part by funds from the U.S. Government (National Institutes of Health-National Cancer Institutes Grant No. RFA CA76639) and the U.S. Government may therefore have certain rights in the invention.

BACKGROUND OF THE INVENTION

The prostate is almost invariably the site of benign and malignant proliferative changes in aging males. Prostatic intraepithelial neoplasia (PIN) develops into prostate cancer in a significant percentage of men, thereby indicating that it might be a premalignant lesion (Bostwick D G and Brawer M K, Cancer 59:788-794, 1987). The relationship between PIN and prostate cancer has been reported in multiple studies (Sakr W A, Grignon D J, Crissman J D, Heilbrun L K, Cassin B J, Pontes J J, Haas G P, In Vivo 8:439-443, 1994; Bostwick D G, Qian J, Am J Surg Pathol 19:506-518, 1995(b); Arakawa A, Song S, Scardino P T, Wheeler T M, Pathol. Res. Pract. 191:868-872, 1995; Qian J, Bostwick D G, Pathol. Res. Pract. 191:860-867, 1995; Qian J, Wollan P, Bostwick D G, Hum. Pathol. 28:143-148, 1997). In fact, the multifocality of PIN within the prostate parallels that of adenocarcinoma and can be traced to the same zones within the gland, for example, the peripheral zone, thus providing a spatial linkage between the two entities (Bostwick, D G, Cancer 75:1823-1836, 1995(a); Kovi J, Mostofi F K, Heshmat M Y, Enterline J P, Cancer 61:555-561, 1988; Bostwick D G, Amin M B, Dundore P, Marsh W, Schultz D S, Hum Pathol. 24:298-310, 1993; Bostwick, D G, Cancer 75:1823-1836, 1995(a); Qian J, Wollan P, Bostwick D G, Hum. Pathol. 28:143-148, 1997). Further, only about one-third of radical prostatectomy specimens have high-grade PIN in both the peripheral and transition zones and when carcinoma is found in the transition zone, there is usually concurrent PIN present.

Data from autopsy studies also supports a relationship between PIN and prostate cancer. For example, in a series of 249 autopsy cases, 77% of prostates with PIN harbored invasive adenocarcinoma, compared to only 24% without PIN (Sakr W A, Grignon D J, Crissman J D, Heilbrun L K, Cassin B J, Pontes J J, Haas G P, In Vivo 8:439-443, 1994). Autopsy studies also demonstrate that development of PIN predates the development of clinically detectable cancer by 5 to 10 years, consistent with the concept that PIN is a pre-malignant lesion (Orozco R, O'Dowd G, Kunnel B, Miller M C, Veltri R W, Urology 51:186-195, 1998). Silvestri et al performed an autopsy study of European men and found an association between PIN and carcinoma in the majority of cases (Silvestri F, Bussani R, Pavletic N, Bassan F, Pathol. Res. Pract. 191: 908-916, 1995). However, more recent analyses have revealed that 70% of autopsy cases with histologic evidence of invasive prostate do not have associated PIN. In a series of 62,537 needle biopsies of the prostate, isolated PIN was found in only 4.1% of cases while invasive cancer was found in 38.3% of cases (Orozco R, O'Dowd G, Kunnel B, Miller M C, Veltri R W, Urology 51:186-195, 1998). Collectively, these findings suggest that a subset of prostate cancers may develop de novo and do not begin with PIN.

Franks (Franks, L. M. (1954) J. Pathol. Bacteriol. 98:617-621) first proposed that atypical hyperplasia was a precursor of prostatic carcinoma. Helpap (Helpap, B. (1980) Virch. Arch. 387:307-31) demonstrated by $^3$H-thymidine uptake that "severe atypical primary hyperplasia is a precancerous lesion". In a key study, McNeal and Bostwick (McNeal et al. (1986) Hum. Pathol. 17:64-71) showed an association between high grade prostatic intraepithelial neoplasia (HG-PIN) and prostatic adenocarcinoma. Bostwick (Bostwick, D. G. et al. (1987) Cancer 59:788-794) subsequently provided a detailed description of the architectural features of HGPIN where he pointed out that >75% of all HGPIN exhibits a dome-like architecture. Since these initial studies, Epstein (Epstein, J. I. et al. (1990) Cancer 65:2321-2327) provided further linkage of HGPIN with organ-confined carcinoma, and multiple studies have now described HGPIN and demonstrated a significant association with cancer. In a series of 249 autopsy cases, 77% of prostates with HGPIN harbored invasive adenocarcinoma, compared to only 24% without HGPIN. Autopsy studies also demonstrated that development of HGPIN predated the development of clinically detectable cancer by 5 to 10 years, consistent with the concept that HGPIN is a pre-malignant lesion. Further, studies have also demonstrated correlation of low-grade prostatic intraepithelial neoplasia (LGPIN) with the development of malignant lesions (Goeman et al. (2003) Prostate Cancer Prostatic Dis. 6:305-10).

Other studies have provided strong support for the association of HGPIN with of the incidence of PCA. For example, a group retrospectively identified 190 men with HGPIN, and 1677 men with only benign prostatic in needle biopsy tissue. The cumulative risk of detection of carcinoma on serial sextant follow-up biopsies was 30.5% for those with isolated HGPIN compared with 26.2% for the control group. HGPIN found on the first repeat biopsy was associated with a 41% risk of subsequent detection of carcinoma compared with an 18% risk if benign prostatic tissue was found on the first repeat biopsy. The results suggest that the risk of prostate carcinoma is 30.5% after a diagnosis of isolated HGPIN in a needle biopsy. Likewise, another group showed that the multiple core involvement by high grade PIN or HGPIN, both on initial and first repeat biopsy, defines a subset of men that are at increased risk of harboring synchronous invasive carcinoma. Other studies have demonstrated that high grade PIN, patient age and PSA are all highly significant predictors of PCA with PIN having the highestrisk ratio. In fact, PIN has been shown to be more predictive of PCA in older patients and those with a serum PSA of >4 ng/ml. Since PIN predates the appearance of PCA by ~2-5 years these reports suggest that patients with high grade PIN need to aggressively monitored for the development of cancer.

A common method of diagnosis for prostate cancer is determining the level of prostate specific antigen (PSA) in the blood. PSA is a glycoprotein secreted by the prostate gland. The PSA test does have limitations of sensitivity and selectivity: in general, levels above 4 ng/ml are suggestive of cancer and levels above 10 ng/ml are highly suggestive. Also, many persons with prostate cancer have normal PSA levels at the time of diagnosis. Therefore, molecular markers with greater sensitivity and selectivity for prostate cancer and the premalignant condition of PIN would be useful for, among other things, the diagnosis of these conditions.

The ATP-binding cassette (ABC) transporter superfamily is one of the largest gene families comprising at least 48 genes and encoding a functionally diverse group of membrane proteins involved in energy-dependent transport of a wide variety of substrates across membranes (Dean et al., Curr Opin Genet Dev, 1995, 5, 779-85). It constitutes a family of proteins that are extremely well conserved during evolution, from bacteria to humans (Ames and Lecar, FASEB J., 1992, 6, 2660-2666). Physiological studies have shown that the prototype ABC protein binds ATP and uses the energy from ATP hydrolysis to drive the transport of various molecules across cell membranes. Most ABC functional proteins from eukaryotes encode a full-transporter, each consisting of two ATP-binding domains (nucleotide binding fold, NBF) and two transmembrane (TM) domains, most of which are arranged in a TM-NBF-TM-NBF fashion (Dean et al., Curr Opin Genet, 1995, 5, 79-785). So far, it is known that the ABC-binding cassette proteins are involved in extracellular and intracellular membrane transport of various substrates, including ions, amino acids, peptides, sugars, vitamins, cholesterol or steroid hormones.

Among the 48 identified human ABC transporter members, 11 have been associated with human disease, including ABCA1, ABCA4 (ABCR) and ABCC7 (CFTR), which are thought to be involved in Tangier disease (Bodzioch M et al., Nat. Genet., 1999, 22(4); 347-351; Brooks-Wilson et al., Nat. Genet., 1999, 22(4), 336-345; Rust S et al., Nat. Genet., 1999, 22, 352-355; Remaley A T et al.,), Stargardt disease (Lewis R A et al., Am. J. Hum. Genet., 1999, 64, 422-434), and cystic fibrosis (Riordan J M et al., Science, 1989, 245, 1066-1073), respectively. These findings imply an important functional role for the ABC gene family. The identification of additional members of this family of genes or the demonstration that one or more of these genes are associated with specific human diseases has tremendous import to the better treatment and management of disease.

Analysis of amino acid sequence alignments of the ATP-binding domains has aided in separating the ABC genes into sub-families (Allikmets et al., Hum Mol Genet, 1996, 5, 1649-1655) according to the Human Genome Gene Organisation (HUGO) classification system. Seven ABC gene subfamilies named ABC A to G have been described in the human genome, e.g., ABCA (ABC1 subfamily), ABCB (MDR/TAP subfamily), ABCC(CFTR/MRP subfamily), ABCD (ALD subfamily), ABCE (OABP subfamily), ABCF (GCN20 subfamily), and ABCG (white subfamily). For the most part, these subfamilies contain genes that also display considerable conservation in the transmembrane domain sequences and have similar gene organization. However, ABC proteins transport various substrates, and some members of different subfamilies have been shown to share more similarity in substrate recognition than do proteins within the same subfamily. Several ABC transport proteins that have been identified in humans are associated with various diseases. Some multiple drug resistance phenotypes in tumor cells have been associated with the gene encoding the MDR (multi-drug resistance) protein, which also has an ABC transporter structure. Other ABC transporters have been associated with neuronal and tumor conditions (U.S. Pat. No. 5,858,719) or potentially involved in diseases caused by impairment of the homeostasis of metals (Biochim Biophys Acta. 1999; 1461 (2):18-404).

The human ABCC subfamily also currently has ten identified members (ABCC1 to 10), seven of which are from the multidrug resistance-like (MRP) subgroup, two from the sulfonylurea receptor (SUR) subgroup, and the CFTR gene. MRP-like proteins are organic anion transporters; e.g., they transport anionic drugs, exemplified by methotrexate (MTX), as well as neutral drugs conjugated to acidic ligands, such as glutathione (GSH), glucuronate, or sulfate, and play a role in resistance to nucleoside analogs (Cui et al., Mol Pharmacol, 1999, 55, 929-37; Kool et al., Proc Natl Acad Sci, 1999, 96, 6914-9; Schuetz et al., Nat Med, 1999, 5, 1048-51; Wijnholds et al., Proc Natl Acad Sci, 2000, 97, 7476-81). More specifically, ABCC1, ABCC2 and ABCC3 transport drugs conjugated to GSH, glucuronate, sulfate and other organic anions, such as MTX, whereas ABCC4 and ABCC5 proteins confer resistance to nucleotide analogs, including PMEA and purine base analogs.

Several genetic variations in some ABCC subfamily members have also been identified as associated with various human inherited diseases. For example, cystic fibrosis is caused by mutations in the ABCC7 gene or CFTR (cystic fibrosis transmembrane conductance regulator) gene (Riordan et al., Science, 1989, 245, 1066-73). Another member of the ABCC subfamily, the ABCC2 gene, has been associated with the Dubin-Johnson syndrome (Wada et al., Hum Mol Genet, 1998, 7, 203-7). Also, mutations in the coding sequence of another gene belonging to the ABCC subfamily, the ABCC6 gene, have been recently identified as responsible for the phenotype of pseudoxanthoma elasticum (Bergen et al., Nat. Genet., 2000, 25, 228-31; Le Saux et al., Nat Genet, 2000, 25, 223-7), which is a genetic disorder of the connective tissue. Likewise, a receptor of sulfonylureas, ABCC8 or SUR1, appears to be involved in familial persistent hyperinsulinemic hypoglycemia of infancy (Thomas et al., Science, 1995, 268, 426-9). The ABCC11 protein, as well as ABCC4 and ABCC5, is smaller than another well-known member of the subgroup, ABCC1 (MRP1), appearing to lack the extra N-terminal domain (Borst et al., J Natl Cancer Inst, 2000, 92, 1295-302), which is however not required for the transport function (Bakos et al., J. Biol. Chem, 1998, 273, 32167-75). Since structurally related ABC proteins often transport similar substrates across the membranes, it would be reasonable to suggest that the ABCC11 protein could share functional similarities with ABCC 4 and/or ABCC5 genes, e.g., the resistance to nucleotide analogs, such as PMEA, and purine base analogs (Schuetz et al., Nat Med, 1999 5, 1048-51; Wijnholds et al., Proc Natl Acad Sci, 2000, 97, 7476-81). Therefore, characterization of a new gene from the ABCC subfamily is likely to yield a biologically important transporter that may have a translocase activity and may play a major role in human pathologies.

The membrane-associated protein encoded by the ABCA5 is a member of the superfamily of ATP-binding cassette (ABC) transporters ABC1 subfamily (U.S. Patent Application Publication Nos. 2002/0123107 and 2003/0044895). It is clustered among 4 other ABC1 family members on 17q24 and it maps to chromosome 17q24.3 (Accession number: NM 172232) in *Homo sapiens*. Gene aliases include ABC13 and EST90625. This cluster of ABCA genes is evolutionarily distinct from that of other ABCA genes, as evidenced by phylogenetic analysis as well as analysis of intron-exon boundaries. The chromosome 17 ABCA genes have 38 exons, whereas the other ABCA genes have 50-52 exons. Therefore, it appears that all of the genes on chromosome 17 arose from an ancestral ABCA gene. This cluster is not represented in plant, nematode, or insect genomes, and there is a single ABCA5-related gene in fish. Thus, ABCA5 appears to be the ancestral gene for this cluster and seems to have arisen early in vertebrate evolution. ABCA5 is expressed as a 6.5-kb mRNA with the highest levels in the human trachea, prostate, testes, uterus and pancreas. Neither the substrate nor the function of the ABCA5 gene has been identified. Alternative splicing of this gene results in several transcript variants, but not all variants have been completely described. For example, transcriptional variant (NM_018672) represents the longer transcript variant. It contains a distinct 5' UTR compared to transcript variant 2, but encodes the same protein.

Despite the foregoing evidence, a considerable controversy remains regarding the importance of PIN as a precursor of PCA. Thus, more work is required to confirm the relationship of PIN with the onset of PCA. More importantly, a specific marker for PIN is required in order to accurately detect PIN in patients. Furthermore, there exists a need in the art for an assay to diagnose PIN, prostate cancer and associated diseases or conditions. The present invention addresses and meets these needs.

SUMMARY OF THE INVENTION

The invention includes an isolated nucleic acid sequence comprising SEQ ID NO:3, wherein the isolated nucleic acid sequence specifically binds with a mammalian ABCA5 polypeptide or fragment thereof. In one aspect, the isolated nucleic acid consists of SEQ ID NO:3.

In one aspect, the isolated nucleic acid sequence is a variant of SEQ ID NO:3, wherein the variant is the same length as SEQ ID NO:3, further wherein the variant has the biological activity of SEQ ID NO:3.

In one aspect, the isolated nucleic acid sequence is a derivative of SEQ ID NO:3, wherein the derivative is at least one nucleic acid residue shorter than SEQ ID NO:3, further wherein the derivative has the biological activity of SEQ ID NO:3.

The invention includes a vector comprising any of the nucleic acid sequences as set forth herein.

The invention also includes an isolated nucleic acid complementary to any of the nucleic acid sequences as set forth herein.

The invention also includes an isolated antibody that specifically binds with a mammalian ABCA5 polypeptide or a fragment thereof. An antibody of the invention may be selected from the group consisting of a polyclonal antibody, a monoclonal antibody, a humanized antibody, a chimeric antibody, and a synthetic antibody. In another aspect, the antibody of the invention binds an ABCA5 polypeptide that is a recombinant polypeptide or a native polypeptide.

The invention includes a method of diagnosing PIN in a mammal, the method comprising obtaining a biological sample from said mammal, determining the level of ABCA5 in the biological sample, and comparing the level of ABCA5 in the biological sample with the level of ABCA5 in a biological sample obtained from a like mammal not afflicted with PIN, wherein a higher level of ABCA5 in the biological sample from the mammal compared with the level of ABCA5 in the biological sample from the like mammal is an indication that the mammal is afflicted with PIN.

In one aspect, the PIN is HGPIN.

A method of diagnosing a pre-PCA condition in a mammal, the method comprising obtaining a biological sample from the mammal, determining the level of ABCA5 in the biological sample, and comparing the level of ABCA5 in a biological sample obtained from a like mammal not afflicted with PIN, wherein a higher level of ABCA5 in the biological sample from the mammal compared with the level of ABCA5 in the biological sample from the like mammal is an indication that the mammal has a pre-PCA condition.

In one aspect, the mammal is a human. In another aspect, the biological sample is selected from the group consisting of a blood sample, a urine sample, a sputum sample, a peritoneal cavity fluid sample, a perineal cavity fluid sample, a pleural cavity fluid sample, a semen sample, a prostatic fluid sample, stool sample and a bone marrow sample. In yet another aspect, the biological sample is selected from the group consisting of a prostate tissue sample, a seminal vesicle tissue sample, a kidney tissue sample, a liver tissue sample, and a testis tissue sample.

In an aspect of the invention, determining the presence or level of ABCA5 in the biological sample is conducted by a method selected from the group consisting of a DNA binding EMSA assay, ELISA, RT-PCR, Northern blot, Western blot and in situ hybridization. In one aspect, a DNA binding EMSA assay or ELISA is performed with at least one reagent selected from the group consisting of a nucleic acid comprising SEQ ID NO:3 and an antibody which specifically binds ABCA5.

The invention includes a method of assessing the effectiveness of a treatment for PIN for prevention of prostate cancer in a mammal, the method comprising assessing the level of an ABCA5 molecule in the mammal before administration of a treatment for PIN to the mammal, and assessing the level of an ABCA5 molecule in the mammal during or after administration of a treatment for PIN to the mammal, wherein a different level of the ABCA5 molecule in the mammal during or after administration of the treatment for PIN than the level of the ABCA5 molecule in the mammal before administration of the treatment for PIN is an indication of the effectiveness of the treatment for PIN in the mammal.

In one aspect of the invention, the PIN is HGPIN.

The invention includes a method of assessing the effectiveness of a treatment for PIN for prevention of a prostate cancer-associated disease or condition in a mammal, the method comprising, assessing the level of an ABCA5 molecule in the mammal before administration of a treatment for PIN to the mammal, and assessing the level of an ABCA5 molecule in the mammal during or after administration of a treatment for PIN to the mammal, wherein a different level of the ABCA5 molecule in the mammal during or after administration of the treatment for PIN than the level of the ABCA5 molecule in the mammal before administration of the treatment for PIN is an indication of the effectiveness of the treatment for PIN in the mammal.

In one aspect, the treatment for PIN is selected from the group consisting of chemotherapy, radiation therapy and surgery.

In an aspect of the invention, the ABCA5 level is assessed by a method selected from the group consisting of a DNA binding assay, RT-PCR, Northern blot, ELISA, Western blot and in situ hybridization.

The invention includes a method of identifying a compound that reduces expression of an ABCA5 molecule in a cell, the method comprising contacting a cell with a test compound and comparing a level of the ABCA5 molecule expression in the cell with a level of an ABCA5 molecule expression in an otherwise identical cell not contacted with the test compound, wherein a higher or lower level of ABCA5 molecule expression in the cell contacted with the test compound compared with the level of ABCA5 molecule expression in the otherwise identical cell not contacted with the test compound is an indication that the test compound reduces expression of the ABCA5 molecule in a cell, thereby identifying a compound that reduces expression of the ABCA5 molecule in a cell.

The invention includes a method of treating HGPIN in a mammal, the method comprising administering to the mammal a molecule that inhibits ABCA5 activity in a cell, thereby treating HGPIN in a mammal. In one aspect, the molecule is selected from the group consisting of a nucleic acid comprising SEQ ID NO:3, a variant of SEQ ID NO:3, a derivative of SEQ ID NO:3, and SEQ ID NO:3.

The invention includes a method of treating HGPIN in a mammal, the method comprising administering to the mammal a molecule identified according to the method of claim 15, thereby treating HGPIN in a mammal.

The invention includes a compound identified by the method of identifying a compound as described herein. In one aspect, the compound is an antibody or an antisense nucleic acid.

The invention includes a kit for diagnosing PIN in a sample obtained from a mammal, the kit comprising a molecule that specifically binds with ABCA5 polypeptide or with a nucleic acid encoding a ABCA5 protein, the kit further comprising an applicator, and an instructional material for the use thereof. In one aspect of the invention, the PIN diagnosed by the kit is HGPIN. In an aspect of the invention, the molecule that specifically binds with an ABCA5 polypeptide is an antibody or a nucleic acid. In one aspect, the nucleic acid comprises SEQ ID NO:3.

The invention includes a kit for treating PIN, the kit comprising a compound that inhibits the expression of ABCA5 and an instructional manual for the use thereof. In an aspect, the compound is an antibody or nucleic acid. In an aspect, the nucleic acid comprises SEQ ID NO:3. In another aspect, the nucleic acid is an antisense nucleic acid.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 illustrates the nucleotide sequence of the recombinant ABCA5 gene (SEQ ID NO:1) cloned from a cDNA expression library utilizing in recognition site probe methods with the PIN specific binding DNA sequence as the probe.

FIG. 2 illustrates the derived amino acid sequence of the ABCA5 gene (SEQ ID NO:2).

FIG. 7 is a summary of EMSA data demonstrating the number of specimens (tissue and urine samples) positive and negative for ABCA5 expression.

FIG. 8 represents the 8 bp nucleic acid sequence (SEQ ID NO.3) of the double stranded sequence that specifically binds the ABCA5 protein.

FIG. 11 is a graph illustrating the expression of ABCA5 using qRT-PCR assays for quantitative detection of ABCA5 mRNA in different human prostate tissue DNA preparations. cDNA equivalent to 50 ng of total RNA was used for each PCR assay. Ct values obtained with different tissues were used to calculate the input amount of template by the calibration curve method. After normalization to the endogenous control, GAPDH (data not shown), these values were expressed relative to the calibrator (tissue with lowest expression) and displayed as relative levels of expression. Values averaged from 3 independent assays+1 S.D. Tissues included: (blue bars, 1-5) 5 different HGPIN; (red bars, 6-7) PCA; (black bars, 8-9) BPH; (bar 10) Seminal Vesicle; (bar 11) Kidney; (bar 12) Testis; (bar 13) Testis Cancer; (bar 14) Liver; (bar 15) Bladder; (bar 16) Kidney cancer; (bar 17) Lung Cancer; (bar 18) Prostate Stroma; and (bar 19) Normal Prostate. ABCA5 primers:

Figure 3:
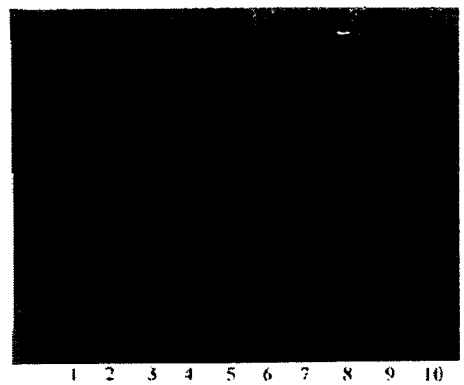
FIG. 3 is an x-ray film image of an electrophoretic mobility shift assay (EMSA) demonstrating binding (band near top of gel) of the $^{32}$P-ATP radiolabeled probe (SEQ ID NO:3) (band at bottom of gel) to the ABCA5 protein in crude protein extracts from seminal vesicle (lanes 1-2), BPH (lanes 3-4), PIN (lanes 5-7), and prostate cancer tissue (lanes 8-10), respectively.
Figure 4:
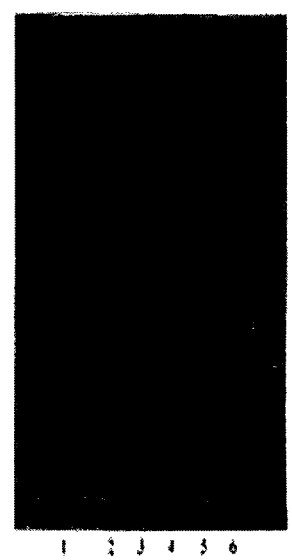
FIG. 4 is an image of a gel from an EMSA demonstrating binding of the $^{32}$P-ATP radiolabeled probe (SEQ ID NO:3) to the ABCA5 protein (band near top of gel) in urine of patients diagnosed with PIN (lanes 1-3, 6) and without PIN (lanes 4-5).

```
Forward:
                                     (SEQ ID NO:4)
5'-3': GGCTGCTATTCTGACCACTCACTATA;

Reverse:
                                     (SEQ ID NO:5)
5'-3': TTAACTGCCCAGACACCATGAT
```

FIG. 12 is a graph illustrating detection of ABCA5 peptide. An ELISA standard curve is illustrated with the ABCA5 peptide (P1) using a rabbit polyclonal antibody raised against P1 (1:5000) and a goat anti rabbit-horse radish peroxidase (1:10,000) secondary antibody.

FIG. 13, comprising FIGS. 13a-b, is as pair of graphs illustrating the ABCA5 levels in urine obtained from patients. FIG. 13a illustrates patients having serum PSA levels of <1.5 ng/ml (■) and >10 ng/ml (▼), respectively. FIG. 13b illustrates patients diagnosed as: normal (n=79), PCA (n=9) and HGPIN (n=107) patients.

DETAILED DESCRIPTION OF THE INVENTION

The present invention is based, in part, on the discovery that ABCA5 is overexpressed in a subject with PIN and, therefore, provides diagnostic methods for detecting and comparing levels of ABCA5 in a biological sample from a subject with PIN. In one embodiment, the subject is a mammal. In a preferred embodiment, the mammal is a human. The present invention also contemplates the use of a novel ABCA5 binding sequence or antibody as a method for assaying ABCA5 expression. The present invention also features methods of altering the levels of ABCA5, for example, in the prostate.

The present invention contemplates further the identification and isolation of a human gene encoding ABCA5 polypeptide of the invention, including a full length, or naturally occurring form of ABCA5 and any antigenic fragments thereof from any animal, particularly mammalian or avian, and more particularly human source. The present invention also contemplates the identification of other DNA binding proteins that would be useful in diagnosing and/or treating PIN and prostate cancer.

According to the present invention, by identifying a marker that is specific for HGPIN, not merely for the prostate, an assay for the ABCA5 protein as set forth herein offers a means to improve on the early detection of pre-malignant prostate cancer (i.e. HGPIN), thereby reducing the need for biopsies when used as an adjunct to current methods. Moreover, a urine assay to detect ABCA5, such as is set forth herein, is convenient and noninvasive, since a needle puncture is not required to collect urine, and therefore can readily be added to existing diagnostic tools.

In accordance with the present invention, conventional molecular biology, microbiology, and recombinant DNA techniques within the skill of the art are used. Such techniques are fully explained in the literature (Sambrook et al., 2001. Molecular cloning a laboratory manual. 3ed. Cold Spring Harbor Laboratory, Cold Spring Harbor, N.Y.; Glover, 1985, DNA Cloning: A practical approach, volumes I and II oligonucleotide synthesis, MRL Press, LTD., Oxford, U.K.; Hames and Higgins, 1985, Transcription and translation; Hames and Higgins, 1984, Animal Cell Culture; Freshney, 1986, Immobilized Cells And Enzymes, IRL Press; and Perbal, 1984, A practical guide to molecular cloning).

DEFINITIONS

As used herein, each of the following terms has the meaning associated with it in this section.

"ABCA5", "normal ABCA5", or "endogenous ABCA5" as the terms are used synonymously herein, refers to the ATP-binding cassette transporter 5 molecule, otherwise known as PIN-1, present in its naturally-occurring state in a mammal.

The articles "a" and "an" are used herein to refer to one or to more than one (e.g., to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |

-continued

| Full Name | Three-Letter Code | One-Letter Code |
|---|---|---|
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"Amplification" refers to any means by which a polynucleotide sequence is copied and thus expanded into a larger number of polynucleotide molecules, e.g., by reverse transcription, polymerase chain reaction, and ligase chain reaction.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device including, but not limited to, a hypodermic syringe, a pipette, and the like, for administering anti-ABCA5 antibodies and the antisense ABCA5 nucleic acid of the invention to a mammal.

By the term "biological activity of SEQ ID NO:3" as used herein is meant the ability of a nucleic acid molecule to bind to an ABCA5 polypeptide. The skilled artisan would further appreciate, based upon the instant disclosure, that the invention is not limited to any particular method of assessing the biological activity of SEQ ID NO:3 and that the invention encompasses any assay to assess the biological activity of SEQ ID NO:3 known in the art or to be developed in the future.

"Biological sample," as that term is used herein, means a sample obtained from a mammal that can be used to assess the level of expression of ABCA5 mRNA, the level of ABCA5 protein present, or both. Such a sample includes, but is not limited to, a blood sample, a prostate tissue biopsy sample, a urine sample, a sputum sample, a peritoneal cavity fluid sample, a perineal cavity fluid sample, a pleural cavity fluid sample, a semen sample, a prostatic fluid sample, a stool sample and a bone marrow sample.

By "complementary to a portion or all of the nucleic acid encoding ABCA5" is meant a sequence of nucleic acid which does not encode an ABCA5 protein. Rather, the sequence which is being expressed in the cells is identical to the non-coding strand of the nucleic acid encoding a ABCA5 protein and thus, does not encode ABCA5 protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand. "Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

By the term "consensus", as used herein, is meant a nucleic acid sequence which has been re-sequenced to resolve un-called bases, or which has been extended using RT-PCR extension kit (such as, e.g., that available from Perkin Elmer, Norwalk, Conn.) in the 5' and/or 3' direction and re-sequenced, or which has been assembled from the overlapping sequences of more that one derived clone (or which have been both extended and assembled).

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A gene encoding the ABCA5 polypeptide of the invention, whether genomic DNA or cDNA, can be isolated from several sources, particularly from a human cDNA or genomic library. Methods for obtaining genes are well known in the art, as described above (see, e.g., Sambrook and Russell, 2001, Molecular Cloning, A Laboratory Approach, Cold Spring Harbor Press, Cold Spring Harbor, N.Y.; Ausubel et al., 2002, Current Protocols in Molecular Biology, John Wiley & Sons, NY; Glover, 1985, DNA Cloning: A practical approach, volumes I and II oligonucleotide synthesis, MRL Press, LTD., Oxford, U.K.; Hames and Higgins, 1985, Transcription and translation; Hames and Higgins, 1984, Animal Cell Culture; Freshney, 1986, Immobilized Cells And Enzymes, IRL Press; and Perbal, 1984, A practical guide to molecular cloning).

Accordingly, any animal cell may potentially be able to serve as the nucleic acid source for the molecular cloning of the ABCA5 gene. The DNA may be obtained by standard procedures known in the art from cloned DNA (e.g., a DNA "library"), and may be obtained from a cDNA library prepared from tissues or cells with high level expression of the protein and/or the transcripts, by chemical synthesis, by cDNA cloning, or by the cloning of genomic DNA, or fragments thereof, purified from the desired cell (Sambrook and Russell, 2001, Molecular Cloning, A Laboratory Approach, Cold Spring Harbor Press, Cold Spring Harbor, N.Y.; Ausubel et al., 2002, Current Protocols in Molecular Biology, John Wiley & Sons, NY; Glover, 1985, DNA Cloning: A practical approach, volumes I and II oligonucleotide synthesis, MRL Press, LTD., Oxford, U.K.; Hames and Higgins, 1985, Transcription and translation; Hames and Higgins, 1984, Animal Cell Culture; Freshney, 1986, Immobilized Cells And Enzymes, IRL Press; and Perbal, 1984, A practical guide to molecular cloning).

A "non-coding" region of a gene consists of the nucleotide residues of the gene (e.g., introns) including 'leader sequences' which are important for mRNA binding to ribosomal proteins involved in mRNA translation to proteins.

"DNA-protein hybridization assays," as used herein, refers to binding assays for identification of protein(s) which bind with specific DNA sequences and for assessing the amounts of protein binding to the DNA.

"Electrophoretic mobility shift assay" or "EMSA", as these terms are used herein, refers to a gel based assay for identification of protein(s) which bind specific DNA sequences and for assessing the amounts of protein binding to the DNA.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, "enzyme linked immuno-sandwich assay" is an antibody based assay used for the identification of protein and for measurements of protein levels in cell or tissue preparations.

By "equivalent" RNA to ABCA5 is meant to include those naturally occurring RNA molecules associated with PIN in various animals, including human. By "complementary" is meant a nucleic acid that can form hydrogen bond(s) with another RNA sequence by either traditional Watson-Crick or other non-traditional types of base-paired interactions.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 500 nucleotides, even more preferably, at least about 500 nucleotides to about 1000 nucleotides, yet even more preferably, at least about 1000 to about 1500, even more preferably, at least about 1500 nucleotides to about 2000 nucleotides, yet even more preferably, at least about 2000 to about 2500, even more preferably, at least about 2500 nucleotides to about 2600 nucleotides, yet even more preferably, at least about 2600 to about 2650, and most preferably, the nucleic acid fragment will be greater than about 2652 nucleotides in length.

As used herein, the term "gene" refers to an assembly of nucleotides that encode a polypeptide, and includes cDNA and genomic DNA.

"Heterologous" DNA refers to DNA not naturally located in the cell, or in a chromosomal site of the cell. The heterologous DNA may include a gene foreign to the cell.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667)). Such proteins (and their encoding genes) have sequence homology, as reflected by their high degree of sequence similarity.

As used herein, an "instruction manual" includes a publication, a recording, a diagram, or any other medium of expression which can be used to communicate the usefulness of the composition of the invention for its designated use. The instruction manual of the kit of the invention may, for example, be affixed to a container which contains the composition or be shipped together with a container which contains the composition. Alternatively, the instruction manual may be shipped separately from the container with the intention that the instructional material and the composition be used cooperatively by the recipient.

The term "isolated" for the purposes of the present invention designates a biological material (nucleic acid or protein) which has been removed from its original environment, that is, the environment in which it is naturally present. For example, a polynucleotide present in the natural state in a plant or an animal is not isolated. The same nucleotide separated from the adjacent nucleic acids in which it is naturally inserted in the genome of the plant or animal is considered as being "isolated." Such a polynucleotide may be included in a vector and/or such a polynucleotide may be included in a composition and remains nevertheless in the isolated state because of the fact that the vector or the composition does not constitute its natural environment.

The "level" of a nucleic acid or polypeptide, as the term is used herein, refers to a measurable amount of a nucleic acid or polypeptide. By way of a non-limiting example, the level of an ABCA5 polypeptide can be ascertained by measuring the concentration of the polypeptide in weight per unit volume. By way of another non-limiting example, the complete absence of an ABCA5 polypeptide from an assay sample can be referred to as a "zero level" of ABCA5 polypeptide in that assay.

"Monte-Carlo-like" screening assay, as used herein, refers to the production of random 7 mer, 8 mer, and 9 mer DNA sequences and protein binding assays employed to identify the 7 mer, 8 mer, and/or 9 mer sequence which binds a DNA-binding protein(s) produced by tumor tissue where the DNA-binding protein is either not produced or produced at a lower level in otherwise identical non-tumor tissue.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is naturally-occurring.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence or coding sequence.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Duplexed DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (e.g., the strand having a sequence homologous to the mRNA). A "recombinant DNA molecule" is a DNA molecule that has undergone a molecular biological manipulation.

The hybridization of SEQ ID NO:3 with SEQ ID NO:2 under high stringency conditions as defined in Sambrook et al., 2001, supra, entails hybridization of a molecule of nucleic acid including SEQ ID NO:3 of varying length from 8 nucleotides to several hundreds of nucleotides with the ABCA5 protein or fragment therein. It goes without saying that the hybridization conditions may be adjusted as a function of the length of the nucleic acid whose hybridization is sought or of the type of labeling chosen, according to techniques known to one skilled in the art. Suitable hybridization conditions may, for example, be adjusted according to the teaching contained in the manual by Sambrook et al. 2001, supra.

The term "nucleotide" designates both the natural nucleotides (A, T, G, C) as well as the modified nucleotides that comprise at least one modification such as (1) an analog of a purine, (2) an analog of a pyrimidine, or (3) an analogous sugar, examples of such modified nucleotides being described, for example, in the PCT application No. WO 95/04064.

A "polynucleotide" means a single strand or parallel and anti-parallel strands of a nucleic acid. Thus, a polynucleotide may be either a single-stranded or a double-stranded nucleic acid.

The term "oligonucleotide" typically refers to short polynucleotides, generally no greater than about 50 nucleotides. It will be understood that when a nucleotide sequence is represented by a DNA sequence (e.g., A, T, G, C), this also includes an RNA sequence (e.g., A, U, G, C) in which "U" replaces "T." As used herein, the term "oligonucleotide" refers to a duplexed nucleic acid (SEQ ID NO:3), generally of at least 7 nucleotides, but preferably 8 nucleotides, that is hybridizable to the ABCA5 protein or fragment therein (SEQ ID NO:2) according to the invention. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of the ABCA5 protein or fragment therein of the invention. In another embodiment, oligonucleotides homologous with the ABCA5 gene (SEQ. ID NO:1) (one or both of which may be labeled) can be used as PCR primers, either for cloning full lengths or fragments of the ABCA5 nucleic acid, or to detect the presence of a nucleic acid encoding the ABCA5 protein. Generally, oligonucleotides are prepared synthetically, such as on a nucleic acid synthesizer. Accordingly, oligonucleotides can be prepared with non-naturally occurring phosphoester analog bonds, such as thioester bonds.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By the term "overexpression of a ABCA5 molecule," as used herein, is meant that the level of expression of the ABCA5 mRNA or protein in a cell is detectably higher or lower than the level of expression of ABCA5 in an otherwise identical cell where the otherwise identical cell is obtained from normal tissue that does not exhibit any detectable disease, disorder or condition associated with or mediated by expression of PIN, such as, but not limited to benign prostate lesions, prostate cancer, other cancers and degenerative disorders such as osteoporesis, immune suppressive disorders or inflammatory disorders.

By the term "PIN", as used herein, is meant prostatic intraepithelial neoplasia (PIN) (Bostwick and Brawer, 1987). The term "PIN" encompasses the various forms and/or degrees of PIN, including, but not limited to, high grade prostatic intraepithelial neoplasia and low grade prostatic intraepithelial neoplasia.

The term "HGPIN" refers to high-grade PIN, or "high grade prostatic intraepithelial neoplasia."

The term "HGPIN" refers to low-grade PIN, or "low grade prostatic intraepithelial neoplasia."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, e.g., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A "protein" is a polypeptide which plays a structural or functional role in a living cell. The polypeptides and proteins of the invention may be glycosylated or unglycosylated.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

The "percentage identity" between two nucleotide or amino acid sequences, for the purposes of the present invention, may be determined by comparing two sequences aligned optimally, through a window for comparison.

The portion of the nucleotide or polypeptide sequence in the window for comparison may thus comprise additions or deletions (for example "gaps") relative to the reference sequence (which does not comprise these additions or these deletions) so as to obtain an optimum alignment of the two sequences.

The percentage is calculated by determining the number of positions at which an identical nucleic base or an identical amino acid residue is observed for the two sequences (nucleic or peptide) compared, and then by dividing the number of positions at which there is identity between the two bases or amino acid residues by the total number of positions in the window for comparison, and then multiplying the result by 100 in order to obtain the percentage sequence identity.

The optimum sequence alignment for the comparison may be achieved using a computer with the aid of known algorithms contained in the package from the company WISCONSIN GENETICS SOFTWARE PACKAGE, GENETICS COMPUTER GROUP (GCG), 575 Science Doctor, Madison, Wis.

By way of illustration, it will be possible to produce the percentage sequence identity with the aid of the BLAST software (versions BLAST 1.4.9 of March 1996, BLAST 2.0.4 of February 1998 and BLAST 2.0.6 of September 1998), using exclusively the default parameters (Altschul et al, 1990. Mol. Biol., 215:403-410; Altschul et al, 1997, Nucleic Acids Res., 25:3389-3402). Blast searches for sequences similar/homologous to a reference "request" sequence, with the aid of the Altschul et al. algorithm. The request sequence and the databases used may be of the peptide or nucleic types, any combination being possible.

The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, such as 2 or 3 orders of magnitude, or, for example, 4 or 5 orders of magnitude.

"Recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

A "recombinant polypeptide" is one which is produced upon expression of a recombinant polynucleotide.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (for example, at least about 75%, or at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; Glover et al. (1985). DNA Cloning: A practical approach, volumes I and II oligonucleotide synthesis, MRL Press, Ltd, Oxford, U.K.); Hames and Higgins (1985). Transcription and Translation).

Similarly, in a particular embodiment, two amino acid sequences are "substantially homologous" or "substantially similar" when greater than 30% of the amino acids are identical, or greater than about 60% are similar. In another embodiment, two amino acids who are less than 100% identical may be "functionally identical" in that they perform the same activity or function. The similar or homologous sequences may be identified by alignment using, for example, the GCG (Genetics Computer Group, Program Manual for the GCG Package, Version 7, Madison, Wis.) pileup program.

By the term "specifically binds," as used herein, is meant an antibody which recognizes and binds an epitope of an ABCA5 protein, but does not substantially recognize or bind other molecules in a sample.

By the term "specifically binds," as used herein, is also meant to include an oligonucleotide which recognizes and binds an ABCA5 protein, but does not substantially recognize or bind other molecules in a sample.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

DESCRIPTION OF THE INVENTION

The present invention relates to methods of diagnosing PIN, prostate cancer and/or other diseases, disorders or conditions associated with or mediated by abnormal expression of DNA binding proteins. Specifically, this invention relates to methods of diagnosing PIN by analyzing the expression of ABCA5. This invention also provides a novel ABCA5 binding DNA sequence and antibodies useful for these diagnostic assays.

The invention also relates to methods of developing and evaluating PIN, prostate cancer and/or other diseases, disorders or conditions associated with or mediated by abnormal expression of DNA binding proteins.

The methods of the invention are utilized to analyze the expression of ABCA5 in order to diagnose PIN or other associated diseases or conditions. The methods of the invention can be practiced by obtaining any biological sample, including but not limited to a blood sample, a prostate tissue sample, a urine sample, a sputum sample, a peritoneal cavity fluid sample, a perineal cavity fluid sample, a pleural cavity fluid sample, a semen sample, a prostatic fluid sample, a stool sample and a bone marrow sample. A preferred biological sample is a urine sample. The level of ABCA5 in a sample can be determined either by measuring the levels of the ABCA5 gene and/or peptide sequences.

Isolated Nucleic Acid and Amino Acid Sequences

In one aspect, the present invention includes an isolated nucleic acid encoding an ATP-binding cassette transporter, ABCA5, or a functional fragment thereof. As will be understood by one of skill in the art, ABC transporter molecules are transmembrane proteins that catalyze ATP-dependent transport of endogenous or exogenous substrates across biological membranes. ABC transporters have been associated with the transport of polypeptides, e.g., a neurotoxic polypeptide, which is involved in Alzheimer's disease. In particular, ABC transporters are associated with multidrug resistance found in cells especially, e.g., cells that are refractory to cytotoxic anti-cancer drugs (Borst, P. (1997) Sem. Cancer Bio. 8:131-134).

Accordingly, the ABCA5 transporter molecules of the invention are suitable targets for developing diagnostic reagents and therapeutic agents to control cellular transport related activities in cells, specifically those in the prostate.

In one embodiment, the present invention relates to an ABCA5 nucleic acid comprising SEQ ID NO:1, or a complementary sequence thereof.

The present invention includes an isolated nucleic acid encoding a mammalian ABCA5 molecule, or a fragment thereof, wherein the nucleic acid shares at least about 99.7% homology with a nucleic acid having the sequence of SEQ ID NO:1. The mammal is preferably a human. Preferably, the nucleic acid is about 99.8% homologous, more preferably, and most preferably, about 99.9% homologous to SEQ ID NO:1, disclosed herein. Even more preferably, the nucleic acid is SEQ ID NO:1. The isolated nucleic acid of the invention should be construed to include an RNA or a DNA sequence encoding a mutant ABCA5 protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic acids and the polypeptides encoded thereby, as disclosed herein. Once armed with the present invention, it is readily apparent to one skilled in the art that other nucleic acids can be obtained by following the procedures described herein in the experimental details section for the generation of other nucleic acids and nucleic acid analogs as disclosed herein (e.g., various chemical, synthetic and modifying methods, and the like), and procedures that are well-known in the art or to be developed.

Further, any other number of procedures may be used for the generation of derivative or variant forms of ABCA5 using recombinant DNA methodology well known in the art such as, for example, that described in Sambrook et al. (2001, Molecular Cloning: A Laboratory Manual, Cold Spring Harbor Laboratory Press, New York) and Ausubel et al. (1997, Current Protocols in Molecular Biology, Green & Wiley, New York).

Procedures for the introduction of amino acid changes in a protein or polypeptide by altering the DNA sequence encoding the polypeptide are well known in the art and are also described in Sambrook et al. (2001, supra); Ausubel et al. (1997, supra).

The invention includes a nucleic acid encoding a mammalian ABCA5 wherein a nucleic acid encoding a tag polypeptide is covalently linked thereto. That is, the invention encompasses a chimeric nucleic acid wherein the nucleic acid sequence encoding a tag polypeptide is covalently linked to the nucleic acid encoding a mutant ABCA5 polypeptide. Such tag polypeptides are well known in the art and include, for instance, green fluorescent protein (GFP), myc, myc-pyruvate kinase (myc-PK), $His_6$, maltose biding protein (MBP), an influenza virus hemagglutinin tag polypeptide, a flag tag polypeptide (FLAG), and a glutathione-5-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize ABCA5 within a cell, a tissue, and/or a whole organism (e.g., a mammalian embryo), detect ABCA5 secreted from a cell, and to study the role(s) of ABCA5 in a cell. Further, addition of a tag polypeptide facilitates isolation and purification of the "tagged" protein such that the proteins of the invention can be produced and purified readily.

As will be discussed in more detail below, in certain situations, it may be desirable to inhibit expression of ABCA5 and the invention therefore includes compositions useful for inhibition of ABCA5 expression. Thus, the invention features an isolated nucleic acid complementary to a portion or all of a nucleic acid encoding a mammalian ABCA5 molecule which nucleic acid is in an antisense orientation with respect to transcription. Preferably, the antisense nucleic acid is complementary with a nucleic acid having at least about 99.7% homology with SEQ ID NO:1, or a fragment thereof. Preferably, the nucleic acid is about 99.8% homologous, and most preferably, about 99.9% homologous to a nucleic acid complementary to a portion or all of a nucleic acid encoding a mammalian ABCA5 having the sequence of SEQ ID NO:1, or a fragment thereof, which is in an antisense orientation with respect to transcription. Most preferably, the nucleic acid is complementary to a portion or all of a nucleic acid that is SEQ ID NO:1, or a fragment thereof. Such antisense nucleic acid serves to inhibit the expression, function, or both, of an ABCA5 molecule.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see Cohen, 1989, In: Oligodeoxyribonucleotides, Antisense Inhibitors of Gene Expression, CRC Press, Boca Raton, Fla.; Tullis, 1991, U.S. Pat. No. 5,023,243,) incorporated by reference herein in its entirety.

The invention also includes an isolated polypeptide comprising a mammalian mutant ABCA5 molecule. Preferably, the isolated polypeptide comprising a mammalian mutant ABCA5 molecule is at least about 99.6% homologous to a polypeptide having the amino acid sequence of SEQ ID NO:2, or some fragment thereof. Preferably, the isolated polypeptide is about 99.7% homologous, more preferably, about 99.8% homologous, more preferably, and most preferably, about 99.9% homologous to SEQ ID NO:2, or some fragment thereof. Most preferably, the isolated polypeptide comprising a mutant ABCA5 molecule is SEQ ID NO:2. In one embodiment of the invention, the isolated polypeptide has the following sequence:

The present invention also provides for analogs of proteins or peptides which comprise an ABCA5 molecule as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "derivatives," and "variants" of the peptides of the invention (or of the DNA encoding the same) which derivatives and variants are ABCA5 peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of the mutant ABCA5 peptide of the present invention.

In another embodiment of the invention, the invention encompasses a nucleic acid as set forth in SEQ ID NO:3. In yet another embodiment of the invention, the invention encompasses "derivatives," and "variants" of the DNA set forth in SEQ ID NO:3. Such derivatives and variants are altered in one or more base pairs, such that the resulting nucleic acid is not identical to the sequence set forth in SEQ ID NO:3, but has the same biological property as SEQ ID NO:3 disclosed herein. It will be understood that a derivative or variant of SEQ ID NO:3 may have a greater degree of activity than SEQ ID NO:3, or the derivative or variant of SEQ ID NO:3 may have a lesser degree of activity than SEQ ID NO:3.

Vectors and Recombinant Cells

The present invention also relates to cloning vectors containing a gene encoding analogs and derivatives of the ABCA5 polypeptide and/or an ABCA5 binding sequence of the invention. The production and use of derivatives and analogs related to the ABCA5 protein are within the scope of the present invention. In a specific embodiment, the derivatives or analogs are functionally active, e.g., capable of exhibiting one or more functional activities associated with a full-length, wild-type ABCA5 polypeptide of the invention.

Due to the degeneracy of nucleotide coding sequences, other DNA sequences which encode substantially the same amino acid sequences as that of ABCA5 gene may be used in the practice of the present invention. These include but are not limited to allelic genes, homologous genes from other species, and nucleotide sequences comprising all or portions of ABCA5 gene which are altered by the substitution of different codons that encode the same amino acid residue within the sequence, thus producing a silent change. Likewise, the ABCA5 derivatives of the invention include, but are not limited to, those containing, as a primary amino acid sequence, all or part of the amino acid sequence of the ABCA5 protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs.

A large number of vector-host systems known in the art may be used. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Possible vectors include, but are not limited to, plasmids or modified viruses, but the vector system must be compatible with the host cell used. Examples of vectors include, but are not limited to, Escherichia coli, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. The cloned gene may be contained on a shuttle vector plasmid, which provides for expansion in a cloning cell, e.g., Escherichia coli, and facile purification for subsequent insertion into an appropriate expression cell line, if such is desired. For example, a shuttle vector, which is a vector that can replicate in more than one type of organism, can be prepared for replication in both E. coli and Saccharomyces cerevisiae by linking sequences from an E. coli plasmid with sequences form the yeast 2 m plasmid.

In an alternative method, the desired gene may be identified and isolated after insertion into a suitable cloning vector in a "shot gun" approach. Enrichment for the desired gene, for example, by size fractionation, can be done before insertion into the cloning vector.

The nucleotide sequence coding for the ABCA5 polypeptide or antigenic fragments, derivatives or analogs thereof, or functionally active derivatives, including chimeric proteins thereof, may be inserted into an appropriate expression vector, e.g., a vector which contains the necessary elements for the transcription and translation of the inserted protein-coding sequence. Such elements are termed herein a "promoter." Thus, nucleic acid encoding the ABCA5 polypeptide of the invention are operationally associated with a promoter in an expression vector of the invention. Both cDNA and genomic sequences can be cloned and expressed under control of such regulatory sequences. An expression vector may also include a replication origin.

The necessary transcriptional and translational signals can be provided on a recombinant expression vector, or they may be supplied by a native gene encoding ABCA5 and/or its flanking regions.

A recombinant ABCA5 protein of the invention, or functional fragments, derivatives, chimeric constructs, or analogs thereof, may be expressed chromosomally, after integration of the coding sequence by recombination. In this regard, any of a number of amplification systems may be used to achieve high levels of stable gene expression (See Sambrook et al., 2001, supra).

The cell into which the recombinant vector comprising the nucleic acid encoding the ABCA5 polypeptide or an ABCA5 binding sequence is cultured in an appropriate cell culture medium under conditions that provide for expression of the ABCA5 polypeptide or an ABCA5 binding sequence by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of the ABCA5 polypeptide or an ABCA5 binding sequence maybe controlled by any promoter/enhancer element known in the art, but these regulatory elements must be functional in the host selected for expression. Promoters which may be used to control ABCA5 gene expression include, but are not limited to, the SV40 early promoter region (Benoist and Chambon, 1981 Nature 290:304-310), the promoter contained in the 3' long terminal repeat of Rous sarcoma virus (Yamamoto, et al., 1980 Cell 22:787-797), the herpes thymidine kinase promoter (Wagner et al., 1981 Proc. Natl. Acad. Sci. U.S.A. 78:1441-1445), the regulatory sequences of the metallothionein gene (Brinster et al., 1982 Nature 296:39-42); prokaryotic expression vectors such as the β-lactamase promoter (Villa-Kamaroff, et al., 1978 Proc. Natl. Acad. Sci. U.S.A. 75:3727-3731), or the Tac promoter (DeBoer, et al., 1983 Proc. Natl. Acad. Sci. U.S.A. 80:21-25); see also "Useful proteins from recombinant bacteria" in Scientific American, 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984 Cell 38:639-646; Ornitz et al., 1986 Cold Spring Harbor Symp. Quant. Biol. 50:399-409; MacDonald, 1987); insulin gene control region which is active in pancreatic beta cells (Hanahan, 1985 Nature: 315:115-122), immunoglobulin gene control region which is active in lymphoid cells (Grosschedl et al., 1984 Cell 38:647-658; Adames et al., 1985 Nature 318:533-538; Alexander et al., 1987 Mol. Cell. Biol. 7:1436-1444), mouse mammary tumor virus control region which is active in testicular, breast, lymphoid and mast cells (Leder et al., 1986 Cell 45:485-495), albumin gene control region which is active in liver (Pinkert et al., 1987 Genes and Devel. 1:268-276), alpha-fetoprotein gene control region which is active in liver (Krumlauf et al., 1985 Mol. Cell. Biol. 5:1639-1648; Hammer et al., 1987 Science 235:53-58), alpha 1-antitrypsin gene control region which is active in the liver (Kelsey et al., 1987 Genes and Devel. 1:161-171) beta-globin gene control region which is active in myeloid cells (Mogram et al., 1985 Nature 315:338-340; Kollias et al., 1986 Cell 46:89-94), myelin basic protein gene control region which is active in oligodendrocyte cells in the brain (Readhead et al., 1987 Cell 48:703-712), myosin light chain-2 gene control region which is active in skeletal muscle (Sani, 1985 Nature 314:283-286), and gonadotropic releasing hormone gene control region which is active in the hypothalamus (Mason et al., 1986 Science 234:1372-1378).

Expression vectors containing a nucleic acid encoding the ABCA5 polypeptide or ABCA5 binding sequence of the invention can be identified by five general approaches: (a) polymerase chain reaction (PCR) amplification of the desired plasmid DNA or specific mRNA, (b) nucleic acid hybridization, (c) presence or absence of selection marker gene functions, (d) analyses with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding the ABCA5 polypeptide or an ABCA5 binding sequence is inserted within the "selection marker" gene sequence of the vector, recombinants containing the ABCA5 nucleic acid can be identified by the absence of the ABCA5 gene functions. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, provided that the expressed protein assumes a functionally active conformation.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; See, Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). Yeast expression systems can also be used according to the invention to express the ABCA5 polypeptide. For example, the non-fusion pYES2 vector (XbaI, SphI, ShoI, NotI, GstXI, EcoRI, BstXI, BamHI, SacI, KpnI, and HindIII cloning sit; Invitrogen) or the fusion pYESHisA, B, C (XbaI, SphI, ShoI, NotI, BstXI, EcoRI, BamHII, SacI, KpnI, and HindIII cloning site, N-terminal peptide purified with Pro-Bond resin and cleaved with enterokinase; Invitrogen), to mention just two, can be employed according to the invention.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage for example of the signal sequence) of proteins. Appropriate cell lines or host systems can be chosen to ensure the desired modification and processing of the foreign protein expressed. For example, expression in a bacterial system can be used to produce an nonglycosylated core protein product. However, the transmembrane ABCA5 protein expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, ABCA5 activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE Dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

A cell has been "transfected" by exogenous or heterologous DNA when such DNA has been introduced inside the cell. A cell has been "transformed" by exogenous or heterologous DNA when the transfected DNA effects a phenotypic change. The transforming DNA may be integrated (covalently linked) into chromosomal DNA making up the genome of the cell.

A recombinant protein such as ABCA5 which is expressed as an integral membrane protein can be isolated and purified by standard methods. Generally, the integral membrane protein can be obtained by lysing the membrane with detergents, such as but not limited to, sodium dodecyl sulfate (SDS), Triton X-100 polyoxyethylene ester, Ipagel/nonidet P-40 (NP-40) (octylphenoxy)-polyethoxyethanol, Digoxin, sodium deoxycholate, and the like, including mixtures thereof. Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Alternatively, a nucleic acid or vector according to the invention can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner, et. al. (1987. PNAS 84/7413); Mackey, et al. (1988, Proc. Natl. Acad. Sci. USA, 85:8027-8031); Ulmer et al. (1993, Science, 259:1745-1748). The use of cationic lipids may promote encapsulation of negatively charged nucleic acids, and also promote fusion with negatively charged cell membranes (Felgner et al., 1989, Science, 337:387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly useful in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or nonpeptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid (see U.S. Pat. Nos. 5,693,622, 5,589,466 and 5,580,859). Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, Wu et al., 1992, supra; Wu and Wu, 1988, supra; Hartmut et al., Canadian Patent Application No. 2,012, 311, filed Mar. 15, 1990; Williams et al., 1991, Proc. Natl. Acad. Sci. USA 88:2726-2730). Receptor-mediated DNA delivery approaches can also be used (Curiel et al., 1992, Hum. Gene Ther. 3:147-154; Wu and Wu, 1987, J. Biol. Chem. 262:4429-4432).

Methods

Methods of Diagnosing PIN, Prostate Cancer and/or Other Associated Diseases or Conditions The skilled artisan will readily understand, when armed with the present disclosure and the data disclosed herein, that diagnostics can be developed which are capable of detecting the overexpression of ABCA5 nucleic acid in a mammal. This is because, as demonstrated by the data elsewhere herein, increased expression of ABCA5 in a mammal, when compared to a mammal with normal endogenous ABCA5 expression, is associated with premalignant forms of prostate cancer generally known as PIN. In one aspect, the PIN is HGPIN. In another aspect, the PIN is LGPIN.

Therefore, determining the level of ABCA5 expression in a mammal or cell can be used as a powerful and novel diagnostic technique for the detection of PIN and diagnosis of patients with an increased tendancy to get prostate cancer, and the like. Thus, the present invention further encompasses methods for the diagnosis of PIN and predicting a high potential for a subject to be afflicted with prostate cancer. In all instances recited herein, whether treating or diagnosing PIN or prostate cancer, the most preferred mammal is a human.

In one embodiment, the present invention includes a method of diagnosing PIN in a mammal comprising obtaining a biological sample from the mammal; determining a presence or level of ABCA5 in said biological sample; comparing the level of ABCA5 in the biological sample with the level of ABCA5 in a biological sample obtained from a like mammal not afflicted with PIN, wherein a higher level of ABCA5 in the biological sample from the mammal compared with the level of ABCA5 in the biological sample from the like mammal is an indication that the mammal is afflicted with PIN, thereby diagnosing PIN in the previously undiagnosed mammal.

In another aspect, the invention includes utilizing an ABCA5 binding sequence or an antibody. In one embodiment, the ABCA5 binding sequence consists of the nucleotides TCCAGCGA (SEQ. NO:3). In another embodiment, a nucleotide sequence other than SEQ ID NO:3 binds ABCA5. Based upon the disclosure set forth herein, a skilled artisan would know how to identify said nucleotide sequence. Expression patterns showed that the ABCA5 protein was expressed in all PIN tissues of the human prostate and was not expressed in PCA, BPH, SV or normal tissues.

One skilled in the art would understand, based upon the disclosure provided herein, that there are a wide variety of methods for assessing the level of ABCA5 in a sample. Such methods include, but are not limited to, Real Time PCR, which can quantitatively measure mRNA expression, antibody-based detection methods (e.g., using anti-ABCA5 antibodies in Western blot or other immune-based analyses, such as ELISA or enzyme linked immuno-sandwich assay); methods for assessing the level of ABCA5 expression in a cell and/or tissues (e.g., using polymerase chain reaction (PCR), and Northern blot analysis, and the like), and/or methods such as DNA/protein binding assays (i.e. EMSAs) based on detection of binding with a duplex nucleic acid, e.g., nucleic acid consisting of SEQ ID NO:3 with ABCA5 polypeptide. Thus, methods of detecting PIN, either by detecting a PIN polypeptide or a nucleic acid encoding PIN (e.g., RNA or DNA) are disclosed herein or are well known to those skilled in the art and are encompassed in the present invention. Furthermore, the present invention encompasses similar assays for the detection of a specific protein or nucleic acid in a sample as may be developed in the future.

One of skill in the art will appreciate, when armed with the present disclosure and data herein, that methods for determining the level of ABCA5 include, but are not limited to Western blotting, ELISA, and other immuno-detection assays well known in the art.

In one aspect, the biological sample is selected from the group consisting of a a blood sample, a prostate tissue sample, a urine sample, a sputum sample, a peritoneal cavity fluid sample, a perineal cavity fluid sample, a pleural cavity fluid sample, a semen sample, a prostatic fluid sample, a stool sample, a bone marrow sample, and the like.

The invention includes a method of assessing the effectiveness of a treatment for PIN and/or prostate cancer by measuring ABCA5 expression. The method comprises assessing the level of ABCA5 expression, amount, and/or activity, before, during and after a specified course of treatment for a disease, disorder or condition mediated by or associated with increased ABCA5 expression. This is because, as stated previously elsewhere herein, increased ABCA5 expression, amount and/or activity is associated with or mediates PIN and/or tumor progression.

Thus, assessing the effect of a course of treatment upon ABCA5 expression/amount/activity indicates the efficacy of the treatment such that a lower level of ABCA5 expression, amount, or activity indicates that the treatment method is successful.

In one embodiment, the course of therapy to be assessed can include, but is not limited to, surgery, chemotherapy, radiation therapy, antibody treatments and/or the multiple modes of therapy.

The invention encompasses probes and primers for detecting the expression, amount, or activity of an ABCA5 gene. The skilled artisan, when equipped with the present disclosure and the data disclosed herein, will appreciate that probes are provided that are capable of specifically hybridizing to DNA or RNA of an ABCA5 gene. For purposes of the present invention, probes are "capable of hybridizing" to DNA or RNA of ABCA5 if they hybridize to an ABCA5 gene under conditions of either high or moderate stringency, see Sambrook et al. (2001, Molecular Cloning: A Laboratory Manual, Cold Spring Harbor Laboratory, New York) but not significantly or detectably to an unrelated gene. Preferably, the probe hybridizes to suitable nucleotide sequences under high stringency conditions, such as hybridization in 5×SSPE, 1× Denhardt's solution, 0.1% SDS at 65° C., and at least one wash to remove unhybridized probe in the presence of 0.2× SSC, 1× Denhardt's solution, 0.1% SDS at 65° C. Except as otherwise provided herein, probe sequences are designed to allow hybridization to an ABCA5 gene, but not to DNA or RNA sequences from other genes. The probes are used, for example, to hybridize to nucleic acid that is present in a biological sample, including, but not limited to, blood, cerebrospinal fluid, lymph, or tissue, isolated from a patient. The hybridized probe is then detected, thereby indicating the presence of the desired cellular nucleic acid. The skilled artisan will recognize that the cellular nucleic acid can be subjected to an amplification procedure, such as polymerase chain reaction (PCR), prior to hybridization. Alternatively, an ABCA5 gene can be amplified and the amplified product subjected to DNA sequencing. An ABCA5 gene can be detected by DNA sequence analysis or hybridization with an ABCA5 specific oligonucleotide probe under conditions and for a time sufficient to allow hybridization to the specific allele. Typically, the hybridization buffer can contain tetramethyl ammonium chloride and the like, see Sambrook et al. (2001, Molecular Cloning: A Laboratory Manual, Cold Spring Harbor Laboratory, New York).

Nucleic acid probes of the present invention may be composed of either deoxyribonucleic acids (DNA), ribonucleic acids (RNA), nucleic acid analogues (e.g., peptide nucleic acids), or any combination thereof, and can be as few as about 12 nucleotides in length, usually about 14 to 18 nucleotides in length, and possibly as large as the entire sequence of an ABCA5 gene. Selection of probe size is somewhat dependent upon the use of the probe, and is well within the skill of the art.

Suitable probes can be constructed and labeled using techniques that are well known in the art. Shorter probes of, for example, 12 bases can be generated synthetically and labeled with $^{32}P$ using $T_4$ polynucleotide kinase. Longer probes of about 75 bases to less than 1.5 kb are preferably generated by, for example, PCR amplification in the presence of labeled precursors such as, but not limited to, $[\alpha^{32}P]$ dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells, see Sambrook et al. (2001, Molecular Cloning: A Laboratory Manual, Cold Spring Harbor Laboratory, New York).

Probes can be labeled by a variety of markers, including for example, radioactive markers, fluorescent markers, enzymatic markers, and chromogenic markers. The use of $^{32}P$ is but one example for marking or labeling a particular probe.

It is a feature of this aspect of the invention that the probes can be utilized to detect the presence of a ABCA5 mRNA or DNA within a sample. However, if the relevant sample is present in only a limited number, then it can be beneficial to amplify the relevant sequence so that it may be more readily detected or obtained.

A variety of methods may be utilized in order to amplify a selected sequence, including, for example, RNA amplification (see Lizardi et al., 1988 Bio/Technology 6:1197-1202; Kramer et al., 1989, Nature 339:401-402; Lomeli et al., 1989, Clinical Chem. 35:1826-1831; U.S. Pat. No. 4,786,600), and DNA amplification utilizing ligase chain reaction (LCR) or PCR (U.S. Pat. Nos. 4,683,195, 4,683,202, and 4,800,159) (see also U.S. Pat. Nos. 4,876,187 and 5,011,769, which describe an alternative detection/amplification system comprising the use of scissile linkages), or other nucleic acid amplification procedures that are well within the level of ordinary skill in the art. With respect to PCR, for example, the method can be modified as known in the art. Transcriptional enhancement of PCR can be accomplished by incorporation of bacteriophage T7 RNA polymerase promoter sequences in one of the primary oligonucleotides, and immunoenzymatic detection of the products from the enhanced emitter may be effected using anti-RNA:DNA antibodies (Blais, 1994, Appl. Environ. Microbiol. 60:348-352). PCR can also be used in combination with reverse dot-blot hybridization (Iida et al., 1993, FEMS Microbiol. Lett. 114:167-172). PCR products may be quantitatively analyzed by incorporation of dUTP (Duplaa et al., 1993, Anal. Biochem. 212:229-236), and samples may be filter sampled for PCR-gene probe detection (Bej et al., 1991, Appl. Environ. Microbiol. 57:3529-3534).

The invention encompasses a method of detecting ABCA5 overexpression and therefore diagnosing PIN and/or the potential of patients to develop prostate cancer wherein PCR amplification is used to detect ABCA5 DNA. As an example, a DNA sample is denatured at about 92° C. to about 95° C. in order to generate single-stranded DNA. The DNA sample can be a cDNA generated from RNA. Specific primers are then annealed to the single-stranded DNA at about 37° C. to about 70° C., depending on the proportion of AT/GC in the primers and other factors well known in the art. The primers are extended at about 72° C. with, for example, Taq DNA polymerase or another thermostable DNA polymerase in order to generate the opposite strand to the template. These steps constitute one cycle, which can be repeated in order to amplify the selected sequence. For greater specificity, nested PCR can be performed. In nested PCR, a second amplification is performed using a second set of primers derived from sequences within the first amplified product. The entire coding region of ABCA5 may be amplified from, for example, cDNA using an adequate number of primers to generate fragment lengths that are a convenient size for determining their sequence. The number of primers necessary will be well known to one of skill in the art.

The present invention further includes a method wherein, LCR amplification is utilized for amplification. LCR primers can be synthesized such that the 5' base of the upstream primer is capable of hybridizing to a unique base pair in a desired gene to specifically detect a ABCA5 gene.

Within an embodiment of the present invention, the probes can be used in an automated, non-isotopic strategy wherein target nucleic acid sequences are amplified by PCR, and then desired products are determined by, for example, a calorimetric oligonucleotide ligation assay (OLA) (Nickerson et al., 1990, Proc. Natl. Acad. Sci. USA 81:8923-8927).

Primers for the amplification of a selected sequence should be selected from sequences that are highly specific to ABCA5 and form stable duplexes with the target sequence. As is well known in the art, the primers should also be non-complementary, especially at the 3' end, should not form dimers with themselves or other primers, and should not form secondary structures or duplexes with other regions of DNA. In general, primers of about 18 to about 20 nucleotides are preferred, and can be easily synthesized using techniques well known in the art. PCR products, and other nucleic acid amplification products, may be quantitated using techniques well known in the art (Duplaa et al., 1993, Anal. Biochem. 212:229-236; Higuchi et al., 1993, Bio/Technology 11:1026-1030).

Nucleotide probes and primers hybridizing with a nucleic acid (genomic DNA, messenger RNA, cDNA) according to the invention also form part of the invention.

According to the invention, nucleic acid fragments derived from a polynucleotide comprising any one of SEQ ID NO:1, or of a complementary nucleotide sequence are useful for the detection of the presence of at least one copy of a nucleotide sequence of the ABCA5 gene or of a fragment or of a variant (containing a mutation or a polymorphism) thereof in a sample.

The nucleotide probes or primers according to the invention comprise a nucleotide sequence comprising any one of SEQ ID NO:1, or a complementary nucleotide sequence thereof.

The nucleotide probes or primers according to the invention comprise at least 8 consecutive nucleotides of a nucleic acid comprising any one of SEQ ID NO:1, or a complementary nucleotide sequence.

Nucleotide probes or primers according to the invention may have a length of 10, 12, 15, 18 or 20 to 25, 35, 40, 50, 70, 80, 100, 200, 500, 1000, or 1500 consecutive nucleotides of a nucleic acid according to the invention, in particular of a nucleic acid comprising any one of SEQ ID NO:1, or a complementary nucleotide sequence.

Alternatively, a nucleotide probe or primer according to the invention consists of and/or comprise the fragments having a length of 12, 15, 18, 20, 25, 35, 40, 50, 100, 200, 500, 1000, or 1500 consecutive nucleotides of a nucleic acid according to the invention, more particularly of a nucleic acid comprising any one of SEQ ID NO:1, or a complementary nucleotide sequence.

The definition of a nucleotide probe or primer according to the invention therefore covers oligonucleotides hybridizing, under the high stringency hybridization conditions defined above, with a nucleic acid comprising any one of SEQ ID NO:1, or a complementary nucleotide sequence.

A nucleotide primer or probe according to the invention may be prepared by any suitable method well known to persons skilled in the art, including by cloning and action of restriction enzymes or by direct chemical synthesis according to techniques such as the phosphodiester method by Narang et al. (1979, Methods Enzymol, 68:90-98) or by Brown et al. (1979, Methods Enzymol, 68:109-151), the diethylphosphoramidite method by Beaucage et al. (1981, Tetrahedron Lett, 22: 1859-1862) or the technique on a solid support described in European patent No. EP 0,707,592.

Each of the nucleic acids according to the invention, including the oligonucleotide probes and primers described above, may be labeled, if desired, by incorporating a marker which can be detected by spectroscopic, photochemical, biochemical, immunochemical or chemical means. For example, such markers may consist of radioactive isotopes ($^{32}$P $^{33}$P, $^{3}$H, $^{35}$S), fluorescent molecules (5-bromodeoxyuridine, fluorescein, acetylaminofluorene, digoxigenin) or ligands such as biotin. The labeling of the probes may be carried out by incorporating labeled molecules into the polynucleotides by primer extension, or alternatively by addition to the 5' or 3' ends. Examples of nonradioactive labeling of nucleic acid fragments are described in particular in French patent No. 78 109 75 or in the articles by Urdea et al. (1988, Nucleic Acids Research, 11:4937-4957) or Sanchez-Pescador et al. (1988, J. Clin. Microbiol., 26(10):1934-1938). A method in homogeneous phase based on FRET ("Fluorescence resonance energy transfer") has been described by Chen and Kwok (Nucleic Acids Res. 1997 Jan. 15; 25(2):347-53). According to this method, the amplified fragments of genomic DNA containing polymorphisms are incubated with a primer labeled with fluorescein at the 5' end in the presence of labeled dideoxynucleotide triphosphate and a modified Taq polymerase. The labeled primer is extended by one base by incorporation of the labeled dideoxynucleotide specific for the allele present on the complementary genomic DNA sequence. At the end of this genotyping reaction, the fluorescence intensities for the two labeling compounds for the labeled dideoxynucleotides are directly analyzed without separation or purification. All these steps may be carried out in the same tube and the modifications of the fluorescence signal monitored in real time. According to another embodiment, the extended primer may be analyzed by MALDI-TOF type mass spectrometry. The base located at the level of the polymorphic site is identified by measuring the mass added to the microsequencing primer (Haff and Smirnov, Genome Res. 1997 April; 7(4):378-88; and Haff and Smirnov, Nucleic Acids Res. 1997 Sep. 15; 25(18):3749-50).

Such nucleotide primers may, for example, be immobilized on a support. Furthermore, it is possible to immobilize on a support, for example in an orderly manner, multiple specific primers as described above, each of the primers being suited to the detection of one of the polymorphisms of the ABCA5 gene according to the invention.

Any polymorphisms of the ABCA5 gene according to the invention may be useful as genetic markers in studies of the association between the presence of a given allele in a subject and the predisposition of this subject to a given pathology, for example, PIN.

Other statistical methods using bi-allelic polymorphisms according to the invention are for example those described by Forsell et al. (Biol. Psychiatry, 1997, 42: 898-903), Xiong et al. (Am. J. Hum. Genet., 1999, 64: 629-640), Horvath et al. (Am. J. Hum. Genet., 1998, 63:1886-1897.), Sham et al. (Ann. Hum. Genet., 1995, 59: 323-336) or Nickerson et al. (Genomics, 1992, 12: 377-387).

The nucleotide probes and primers according to the invention may have structural characteristics of the type to allow amplification of the signal, such as the probes described by Urdea et al. (1991, Nucleic Acids Symp Ser., 24:197-200) or alternatively in European patent No. EP-0,225,807.

The oligonucleotide probes according to the invention may be used in particular in Southern-type hybridizations with the genomic DNA or alternatively in northern-type hybridizations with the corresponding messenger RNA when the expression of the corresponding transcript is sought in a sample.

The probes and primers according to the invention may also be used for the detection of products of PCR amplification, RT-PCR amplification or alternatively for the detection of mismatches.

Nucleotide probes or primers according to the invention may be immobilized on a solid support. Such solid supports are well known to persons skilled in the art and comprise surfaces of wells of microtiter plates, polystyrene beads, magnetic beads, nitrocellulose bands or microparticles such as latex particles.

Thus, the probes according to the invention, immobilized on a support, may be ordered into matrices such as "DNA chips." Such ordered matrices have in particular been described in U.S. Pat. No. 5,143,854, in published PCT applications WO 90/15070 and WO 92/10092.

Support matrices on which oligonucleotide probes have been immobilized at a high density are for example described in U.S. Pat. No. 5,412,087 and in published PCT application WO 95/11995.

Method of Isolating ABCA5 Protein from a Subject

The invention further provides methods of isolating an ABCA5 protein. As shown herein in the examples, ABCA5 is associated with PIN. Thus, ABCA5 protein can be isolated from a patient with PIN by use of an antibody or a protein binding DNA sequence (e.g., SEQ ID NO:3). The biological sample used in the practice of this method can be any described herein. In one embodiment, the biological sample is a urine sample or a blood sample.

The present invention relates to an antibody directed against a polypeptide comprising an amino acid sequence of the SEQ ID NO:2; a polypeptide fragment or variant of a polypeptide comprising an amino acid sequence of the SEQ ID NO:2, or a polypeptide termed "homologous" to a polypeptide comprising amino acid sequence selected from SEQ ID NO:3, also forms part of the invention, as produced in the trioma technique or the hybridoma technique described by Kozbor et al. (1983, Hybridoma, 2(1):7-16).

Thus, the subject of the invention is, in addition, a method of detecting the presence of a polypeptide according to the invention in a sample, said method comprising the steps of bringing the sample to be tested into contact with an antibody directed against a polypeptide comprising an amino acid sequence of the SEQ ID NO:2, a polypeptide fragment or variant of a polypeptide comprising an amino acid sequence of the SEQ ID NO:2, or a polypeptide termed "homologous" to a polypeptide comprising amino acid sequence of SEQ ID NO:2, and detecting the antigen/antibody complex formed.

Antibodies against ABCA5 are made by methods known to the skilled artisan, and summarized as follows.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Human monoclonal antibodies may be prepared by the method described in U.S. patent publication 2003/0224490. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory Press, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105).

A preferred method of co-immunoprecipitation is described in the examples herein. See also Harlow et al., (1988, Antibodies: A Laboratory Manual, Cold Spring Harbor Laboratory Press, Cold Spring Harbor, N.Y.) and Harlow et al., (1999, Using Antibodies: A Laboratory Manual, Cold Spring Harbor Laboratory Press, Cold Spring Harbor, N.Y.).

Various procedures known in the art may be used for the production of polyclonal antibodies to the ABCA5 polypeptide or derivative or analog thereof. For the production of antibody, various host animals can be immunized by injection with the ABCA5 polypeptide, or a derivatives (e.g., fragment or fusion protein) thereof, including but not limited to rabbits, mice, rats, sheep, goats, etc. In one embodiment, the ABCA5 polypeptide or a fragment thereof can be conjugated to an immunogenic carrier, e.g. bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the ABCA5 polypeptide, or a fragment, analog, or derivative thereof, any technique that provides for the production of antibody molecules by continuous cell lines in culture may be used. These include but are not limited to the hybridoma technique originally developed by Kohler and Milstein (1975, Nature, 256:495-497), as well as the trioma technique, the human B-cell hybridoma technique (Kozbor et al., 1983, Immunology Today, 4:72; Cote et al., 1983, Proc. Natl. Acad. Sci. U.S.A., 80:2026-2030), and the EBV-hybridoma technique to produce human monoclonal antibodies (Cole et al., 1985, In: Monoclonal Antibodies and Cancer Therapy, Alan R. Liss, Inc., pp. 77-96). In an additional embodiment of the invention, monoclonal antibodies can be produced in germ-free animals (WO 89/12690). In fact, according to the invention, techniques developed for the production of "chimeric antibodies" (Morrison et al., 1984, J. Bacteriol. 159:870; Neuberger et al., 1984, Nature, 312:604-608; Takeda et al., 1985, Nature 314:452-454) by splicing the genes from a mouse antibody molecule specific for the ABCA5 polypeptide together with genes from a human antibody molecule of appropriate biological activity can be used; such antibodies are within the scope of this invention. Such human or humanized chimeric antibodies may be used in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476,786 and 5,132,405 to Huston; U.S. Pat. No. 4,946,778) can be adapted to produce ABCA5 polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the ABCA5 polypeptide, or its derivative, or analog.

Antibody fragments which contain the idiotype of the antibody molecule can be generated by known techniques. For example, such fragments include but are not limited to: the F(ab') fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays (see Methods in Molecular Biology, Vol. 149; The ELISA Guidebook by John R. Crowther, Humana Press, Totowa, N.J., 2001), immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of the ABCA5 polypeptide, one may assay generated hybridomas for a product which binds to the ABCA5 polypeptide fragment containing such epitope. For selection of an antibody specific to the ABCA5 polypeptide from a particular species of animal, one can select on the basis of positive binding with the ABCA5 polypeptide expressed by or isolated from cells of that species of animal.

The foregoing antibodies can be used in methods known in the art relating to the localization and activity of the ABCA5 polypeptide (e.g., for Western blotting) ABCA5 polypeptide in situ, measuring levels thereof in appropriate physiological samples, etc. using any of the detection techniques mentioned above or known in the art.

In a specific embodiment, antibodies that agonize or antagonize the activity of the ABCA5 polypeptide can be generated. Such antibodies can be tested using the assays described infra for identifying ligands.

The invention also relates to single-chain Fv antibody fragments (ScFv) as described in U.S. Pat. No. 4,946,778 or by Martineau et al. (1998, J Mol Biol, 280(1):117-127).

The antibodies according to the invention also comprise antibody fragments obtained with the aid of phage libraries as described by Ridder et al., (1995, Biotechnology (NY), 13(3):255-260) or humanized antibodies as described by Reinmann et al. (1997, AIDS Res Hum Retroviruses, 13(11):933-943) and Leger et al., (1997, Hum Antibodies, 8(1):3-16).

The antibody preparations according to the invention are useful in immunological detection tests intended for the identification of the presence and/or of the quantity of antigens present in a sample.

An antibody according to the invention may comprise, in addition, a detectable marker which is isotopic or nonisotopic, for example fluorescent, or may be coupled to a molecule such as biotin, according to techniques well known to persons skilled in the art.

Methods of Modulating Levels of ABCA5

The instant invention includes methods of halting the progression of PIN or the progression of PIN to prostate cancer or the recurrence or PIN or prostate cancer following therapeutic treatment by modulating the level of ABCA5 mRNA or protein in the prostate and/or in the PIN lesion. As shown in the examples herein, ABCA5 is overexpressed in patients with PIN. Therefore, in one embodiment, the method of decreasing the level of ABCA5 would be advantageous. In one aspect, the invention provides a method of a method of identifying a compound that reduces expression of an ABCA5 molecule in a cell(s) comprising contacting a cell(s) with a test compound and comparing a level of the ABCA5 molecule expression in said cell with a level of an ABCA5 molecule expression in an otherwise identical cell(s) not contacted with the test compound, wherein a higher or lower level of ABCA5 molecule expression in the cell(s) contacted with the test compound compared with the level of ABCA5 molecule expression in the otherwise identical cell not contacted with the test compound is an indication that the test compound reduces expression of the ABCA5 molecule in a cell, thereby identifying a compound that reduces expression of the ABCA5 molecule in a cell.

Decreasing the level of ABCA5 protein can be accomplished by any method known to the skilled artisan. Examples of methods to decrease the level of ABCA5 protein include, but are not limited to: decreasing expression of an endogenous ABCA5 gene, decreasing expression of ABCA5 mRNA, and increasing degradation of the ABCA5 protein.

Decreasing expression of an endogenous ABCA5 gene includes providing a specific inhibitor of ABCA5 gene expression. Decreasing expression of ABCA5 mRNA includes decreasing the half-life or stability of specifically localized ABCA5 mRNA or decreasing expression of ABCA5 mRNA. Methods of decreasing expression of ABCA5 mRNA include, but are not limited to, methods using siRNA, antisense, ribozymes and other specific inhibitors of ABCA5 mRNA expression.

In a preferred embodiment, siRNA is used to decrease the level of ABCA5 protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14(7):255-258; David R. Engelke, Ed., RNA Interference (RNAi) Nuts & Bolts of RNAi Technology, DNA Press (2003); and Gregory J. Hannon, Ed., RNAi A Guide to Gene Silencing, Cold Spring Harbor Laboratory Press (2003). Soutschek et al. (2004, Nature 432:173-178) describe a chemical modification to siRNAs that aids in intravenous systemic delivery. Therefore, the present invention also includes methods of decreasing levels of ABCA5 protein by using RNAi technology.

Inhibitors of endogenous ABCA5 gene expression or of ABCA5 mRNA expression can be identified by screening test compounds for the capacity to reduce or preclude ABCA5 gene expression or ABCA5 mRNA expression in a cell. The ABCA5 coding sequence in such screening assays may include an in-frame fusion of a tag to the ABCA5 coding sequence. Such tags enable monitoring of ABCA5 expression by antibody detection of the tags or spectral methods of detection (e.g., fluorescence or luminescence). Test compounds for use in such screening methods can be small molecules, nucleic acids, peptides, peptidomimetics and other drugs. The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145).

ABCA5 protein levels can also be reduced by the expression of an intracellular antibody ("intrabody") against ABCA5 protein from an expression vector. Expression vectors and methods of transfection with them are discussed elsewhere herein. Alternatively, mRNA encoding an intrabody against ABCA5 protein can be introduced locally into a cell using the photoporation method disclosed herein.

The invention also features inhibitors of ABCA5 protein, wherein such inhibitors are based on the nucleic acid sequence set forth in SEQ ID NO:3. As described in detail elsewhere herein, nucleic acids can be used to inhibit the activity of ABCA5 directly (e.g., direct binding) and/or to inhibit the activity of ABCA5 indirectly (e.g., by decreasing expression of ABCA5 or by increasing expression of a separate ABCA5 inhibitor).

Accordingly, many methods of the invention related to the use of nucleic acids to inhibit ABCA5 are equally applicable to the inhibition of ABCA5 through SEQ ID NO:3. By way of a non-limiting example, a nucleic acid construct comprising SEQ ID NO:3 my be inserted into a cell, and the production of additional SEQ ID NO:3 nucleic acids therefrom, regulated in order to inhibit ABCA5. Other methods of using nucleic acids including SEQ ID NO:3, as well as variants and derivatives of SEQ ID NO:3, to inhibit ABCA5 are described elsewhere herein, and will be apparent to the skilled artisan when equipped with the present disclosure.

The invention also encompasses the use of pharmaceutical compositions of an appropriate antibody, protein or peptide, mimetope, peptidomimetic, and/or isolated nucleic acid to practice the methods of the invention, the compositions comprising an appropriate antibody, protein or peptide, mimetope, peptidomimetic, and/or isolated nucleic acid and a pharmaceutically-acceptable carrier.

As used herein, the term "pharmaceutically-acceptable carrier" means a chemical composition with which an appropriate antibody, protein or peptide, mimetope, peptidomimetic, and/or isolated nucleic acid may be combined and which, following the combination, can be used to administer the appropriate antibody, protein or peptide, mimetope, peptidomimetic, and/or isolated nucleic acid to a mammal.

The therapeutic methods of the invention thus encompass the use of pharmaceutical compositions of an appropriate small molecule, protein or peptide and/or isolated nucleic acid to practice the methods of the invention.

The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 micromolar and 10 micromolar in a mammal.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers and AZT, protease inhibitors, reverse transcriptase inhibitors, interleukin-2, interferons, cytokines, and the like.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Methods of Identifying Useful Compounds

The present invention further includes a method of identifying a compound that affects expression of ABCA5 in a cell. The method comprises contacting a cell with a test compound and comparing the level of expression of ABCA5 in the cell so contacted with the level of expression of ABCA5 in an otherwise identical cell not contacted with the compound. If the level of expression of ABCA5 is higher or lower in the cell contacted with the test compound compared to the level of expression of ABCA5 in the otherwise identical cell not contacted with the test compound, this is an indication that the test compound affects expression of ABCA5 in a cell.

One skilled in the art would appreciate, based upon the disclosure provided herein, that assessing the level of ABCA5 can be performed using probes (e.g., antibodies and/or nucleic acid probes that specifically bind with ABCA5 gene or protein), such that the method can identify a compound that selectively affects expression of ABCA5. Such compounds are useful for inhibiting expression of ABCA5. One skilled in the art would understand that such compounds can be useful for inhibiting a disease, disorder, or condition mediated by and/or associated with increased expression of ABCA5, e.g., increased levels of ABCA5 is associated with PIN. Also, the levels of ABCA5 activity by cells can be measured by evaluation of Hoechst 3332 dye (Sandoz, Basel, Switzerland) uptake and retainance. Thus, the skilled artisan would appreciate, based on the disclosure provided herein, that it may useful to decrease expression of ABCA5.

The skilled artisan will further appreciate that the present invention is not limited to a method of identifying a useful compound in a cell or an animal. That is, the present invention includes methods of identifying a useful compound in a cell-free system. A cell-free system, as used herein, refers to an in vitro assay wherein the components necessary for a reaction to take place are present, but are not associated with a cell. Such components can include cellular enzymes, transcription factors, proteins, nucleic acids, and the like, provided that they are substantially free from a cell. Thereby, the present invention includes a method of identifying a useful compound for treating PIN and preventing the progression of PIN to prostate cancer or an associated disease or condition.

One skilled in the art would appreciate, based on the disclosure provided herein, that the level of expression of ABCA5 in the cell may be measured by determining the level of expression of mRNA encoding ABCA5 or ABCA5 protein itself. Alternatively, the level of expression of ABCA5 can be determined by using immunological methods to assess ABCA5 production using anti-ABCA5 antibodies. Further, nucleic acid-based detection methods, such as Northern blot and PCR assays and the like, can be used as well. In addition, the level of ABCA5 activity in a cell can also be assessed by determining the level of various parameters which can be affected by ABCA5 activity, such as, for example, Hoechst 3332 uptake, PIN cell proliferation/survival and PIN volume. Thus, one skilled in the art would appreciate, based upon the disclosure and reduction to practice provided herein, that there are a multitude of methods that are well-known in the art which can be used to assess the level of ABCA5 activity in a cell including those disclosed herein and others which may be developed in the future.

In addition, a protein that specifically binds with ABCA5 can be identified using, for example, a yeast two hybrid assay. Yeast two hybrid assay methods are well-known in the art and can be performed using well documented techniques, for example those described in Bartel and Fields, (The Yeast Two-Hybrid System, Oxford University Press, Cary, N.C.). Therefore, once armed with the teachings provided herein, e.g., the full amino and nucleic acid sequences of the ABCA5 protein, one skilled in the art can easily identify a protein that specifically binds with ABCA5.

One skilled in the art would understand, based upon the disclosure provided herein, that the invention encompasses any molecule identified using the methods discussed elsewhere herein. That is, molecules that associate with ABCA5 or an ABCA5 target protein, can be used to develop therapeutics and diagnostics for diseases, disorders or conditions mediated by ABCA5. That is, one skilled in the art would appreciate, as more fully set forth elsewhere herein in discussing antibodies that specifically bind with ABCA5, that a ABCA5-associated protein can be used to develop therapeutics that inhibit ABCA5 activity in a cell by inhibiting ABCA5 expression and, therefore, ABCA5 binding interactions and/or ABCA5 activity.

ABCA5-associated proteins identified by the above-disclosed methods can be used directly to inhibit ABCA5 interactions by contacting a cell with the ABCA5-associated protein, or a portion thereof, or they can be used to develop antibodies and/or peptidomimetics that can inhibit the ABCA5-associated protein interaction with ABCA5 thereby inhibiting ABCA5 function, activity, and cleavage. Thus, ABCA5-associated proteins are useful and are encompassed by the invention.

Kits

The present invention also provides kits useful in practicing the methods of the invention.

The present invention encompasses various kits which comprise a compound, including a nucleic acid encoding ABCA5, an ABCA5 polypeptide, an antibody that specifically binds ABCA5, a nucleic acid complementary to a nucleic acid encoding ABCA5 but in an antisense orientation, an applicator, and instruction manual which describe use of the compound to perform the methods of the invention. Although model kits are described below, the contents of other useful kits will be apparent to the skilled artisan in light of the present disclosure. Each of these kits is contemplated within the present invention.

In one aspect, the invention includes a kit for treating PIN and preventing the development of prostate cancer and/or associated diseases or conditions. The kit is used in the same manner as the methods disclosed herein for the present invention. Briefly, the kit may be used to contact a cell with a nucleic acid encoding an ABCA5 molecule of the invention. Additionally, the kit comprises an applicator and an instruction manual for the use of the kit. These instructions simply embody the examples provided herein.

The kit further includes a pharmaceutically-acceptable carrier. The composition is provided in an appropriate amount as set forth elsewhere herein. Further, the route of administration and the frequency of administration are as previously set forth elsewhere herein.

In another aspect, the invention includes a kit for treating PIN and preventing prostate cancer and/or associated diseases or conditions. The kit is used in the same manner as the methods disclosed herein for the present invention. Briefly, the kit may be used to contact a cell with an inhibitor of ABCA5. Additionally, the kit comprises an applicator and an instruction manual for the use of the kit. These instructions simply embody the examples provided herein. The kit further includes a pharmaceutically-acceptable carrier. The composition is provided in an appropriate amount as set forth elsewhere herein. Further, the route of administration and the frequency of administration are as previously set forth elsewhere herein.

The invention further encompasses a kit for the treatment of PIN and the prevention of prostate cancer and/or associated diseases or conditions. The skilled artisan will appreciate that the kit can be used according to the methods set forth herein. The kit comprises an antibody, small molecule, or peptide that binds ABCA5, or some fragment thereof, an applicator, and an instruction manual substantially similar to the examples provided herein. The kit further includes a pharmaceutically acceptable carrier, of which the composition, route of administration, and frequency of administration are as previously disclosed elsewhere herein.

Further, the invention comprises a kit for treating PIN and preventing prostate cancer and/or associated diseases or conditions comprising an antisense nucleic acid complementary to a nucleic acid encoding a mammalian ABCA5 molecule, or some fragment thereof. Such kits can be used according to the methods of the invention to mediate the decreased expression of ABCA5. Additionally, the kit comprises an applicator and an instruction manual for the use of the kit. These instructions simply embody the examples provided herein. The kit further includes a pharmaceutically-acceptable carrier. The antisense nucleic acid and pharmaceutically-acceptable carrier are provided in an appropriate amount as set forth elsewhere herein. Further, the route of administration and the frequency of administration are as previously set forth elsewhere herein.

The present invention further encompasses a kit for detecting the presence of a nucleic acid according to the invention in a sample. Briefly, the kit comprises one or more nucleotide probe(s) or primer(s) as described above, where appropriate, the reagents necessary for the hybridization reaction. In one embodiment, the kit comprises a probe consisting of SEQ ID NO:3. In one embodiment, the detection kit is characterized in that the probe(s) or primer(s) are immobilized on a support.

In another embodiment, the detection kit is characterized in that the oligonucleotide probes comprise a detectable marker. In another embodiment, the detection kit described above, such a kit will comprise a plurality of oligonucleotide probes and/or primers in accordance with the invention which may be used to detect a target nucleic acid of interest or alternatively to detect mutations in the coding regions or the non-coding regions of the nucleic acids according to the invention, more particularly of nucleic acids comprising any one of SEQ ID NO:1, or a complementary nucleotide sequence. Alternatively, the target nucleic acid is a nucleic acid fragment or variant of a nucleic acid comprising any one of SEQ ID NO:1, or of a complementary nucleotide sequence.

The present invention further encompasses a kit for detecting PIN according to the invention in a sample. Briefly, the kit comprises one or more nucleotide probe(s) or primer(s) as described above, where appropriate, the reagents necessary for the hybridization reaction. In one embodiment, the kit comprises a probe consisting of SEQ ID NO:3. In one embodiment, the detection kit is characterized in that the probe(s) or primer(s) are immobilized on a support. In another embodiment, the detection kit is characterized in that the oligonucleotide probes comprise a detectable marker. In another embodiment, the detection kit described above, such a kit will comprise a plurality of oligonucleotide probes and/or primers in accordance with the invention which may be used to detect a target nucleic acid of interest or alternatively to detect mutations in the coding regions or the non-coding regions of the nucleic acids according to the invention, more particularly of nucleic acids comprising any one of SEQ ID NO:1, or a complementary nucleotide sequence. Alternatively, the target nucleic acid is a nucleic acid fragment or variant of a nucleic acid comprising any one of SEQ ID NO:1, or of a complementary nucleotide sequence.

In one aspect of the invention, a kit is provided for the detection of PIN in a patient. In another aspect, a kit is provided for the detection of HGPIN in a patient. In yet another aspect, a kit is provided for the detection of LGPIN in a patient.

The present invention also encompasses a kit for amplifying a nucleic acid according to the invention, and more particularly a nucleic acid comprising any one of SEQ ID NO:1, or a complementary nucleotide sequence, or as depicted in any one of SEQ ID NO:1, or of a complementary nucleotide sequence. Briefly, the kit comprises a pair of nucleotide primers in accordance with the invention, whose hybridization position is located respectively on the 5' side and 3' side of the target nucleic acid whose amplification is sought; and optionally, reagents necessary for the amplification reaction. In one embodiment, the kit may comprise at least one pair of nucleotide primers as described above.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Materials and Methods

Tissue Samples:

Prostates were obtained fresh within 1 hr of surgery, cut in thick sagittal slices and pieces dissected out from different regions for whole mount frozen sections. Tissues containing PIN and Prostate Cancer were identified by hematoxylin and eosin (H&E) staining and the specimens (~200 mg/specimen) carefully dissected to remove other material prior to mincing of the tissue. To prepare nuclear protein extracts, the minced tissue was processed according to methods previously described (Wang, M., Hu, Y., Shima, I., and Stearns, M. E. Identification of positive and negative regulator elements for the Tissue Inhibitor of Metalloproteinase 1 gene. *Oncol. Res* 10, 219-233 (1998)) which were modified from Singh et al. (Singh, H., J. H. Lebowitz, A. S. Baldwin, and Sharp, P. A. (1988)).

In some methods, after surgical removal, human prostates were collected within 30 minutes and dissected to remove pieces of tissue containing prostate carcinoma (PCA), high grade prostatic intraepithelial neoplasia (HGPIN), stroma, benign prostatic hyperplasia (BPH) and seminal vesicles (SV). The diagnosis of these tissue was confirmed by H&E stained sections. In addition, prostate tissue with histologically-confirmed HGPIN (n=10) was purchased from a private vendor [Collaborative Genomics, Inc., Boston, Mass.]. Protein extracts were prepared from tissue samples (~100-200 mg) containing at least 80% HGPIN and no evidence of PCA using a modification of the method of Singh et al. (23) as previously described elsewhere (24). In brief, tissue was washed 3 times with PBS and the tissue were cut to small piece then suspended in 2 ml cold buffer A (10 mM HEPES pH 7.9, 10 mM KCl, 0.1 mM EDTA, 0.1 mM EGTA, 1 mM DTT, 0.5 mM PMSF). The pellet was sonicated for 30 sec. and centrifuged (10,000 rpm for 15 min.). The supernatant was collected and the protein precipitated with 4 volumes of cold acetone (−20° C.). The protein was then snap frozen in liquid nitrogen and stored at −800 C for less than 1 year. For DNA binding assays, the samples were thawed and 2 μL of the protein extract (~5 μg protein) incubated with 1 μg of poly (dI-dC) for 15 min, followed by incubation with the $P^{32}$-labeled DNA probe (~100,000 dpm) for 30 min. at 40° C. DNA binding to the protein(s) was then visualized using gel electrophoresis.

Identification of the Double Stranded DNA Sequence:

A 'Monte Carlo' like screening assay was developed for the detection of novel nuclear proteins associated with human prostate cancer (International Application No. PCT/US03/14098 of Stearns et al.). In brief, the basic assay involved the synthesis of a set of DNA sequences and comparisons of the relative activity of probe and protein binding from PIN tissue and prostate cancer tissue (i.e. measured by x-ray imaging of the amount of $^{32}$P-labeled DNA binding to protein on polyacrylamide gels in electrophoretic mobility assays or EMSAs). By this approach the TCCAGCGA (SEQ ID NO:3) sequence was identified which specifically binds the ABCA5 protein with high affinity.

PIN-specific cDNA Expression Library:

mRNA was isolated from freshly dissected HGPIN tissue according to the protocol described by PolyATtract System 1000 (Promega). A phage vector-ZAP Expression vector (Stratagene) was used and construction of the cDNA library was according to a protocol of the ZAP Express cDNA Synthesis Kit and ZAP Express cDNA Gigapack III Gold Cloning Kit (Promega).

EMSA:

Electrophoresis mobility shift assays were carried out as previously described by Sambrook et al. (Sambrook, J., E. D. Fritsch, and Maniatis, *T. Molecular cloning. A laboratory manual. 2nd edition. Cold Spring Harbor Laboratory Press.* Vol 1, pp 2.82-82.108 (1989) utilizing constant amounts of nuclear protein extract (~5 μg) (unless otherwise stated) incubated with 1 μg polydIdC for 15 min. on ice, then incubated with the $P^{32}$-labeled probe (10 ng DNA) for 30 min. prior to electrophoresis using standard methods (Singh, H., J. H. Lebowitz, A. S. Baldwin, and Sharp, P. A. (1988). Protein binding to the DNA probe was measured by x-ray imaging according to methods of Sambrook et al.

Cloning of the ABCA5 Gene:

'DNA-protein' hybridization assays were carried out on a phagemid expression cDNA library with a $^{32}$P-labeled oligonucleotide (~100,000 cpm) which contained the TCCAGCGA sequence. The clones identified were subcloned in three successive cycles and re-probed with the $^{32}$P-labeled TCCAGCGA (SEQ ID NO:3) probe. EMSAs with protein extracts from the recombinant ABCA5 clone (5 μg/ml) and the $^{32}$P-labeled TCCAGCGA (SEQ ID NO:3) probe (~100,000 cpm) revealed a single 'band shift'. The crude protein extracts from host bacteria XL-1 blue MRF infected by wild type phage (lambda C1857 Sam7) did not exhibit any detectable band shift when incubated with the probe. Cold competition assays confirmed with the unlabeled TCCAGCGA (SEQ ID NO:3) probe confirmed that the recombinant ABCA5 protein (~105 Kda) specifically binds the TCCAGCGA (SEQ ID NO:3) probe.

The gene was excised and sequenced by the Molecular Biology Sequencing Facility (Univ. of Pennsylvania, Philadelphia). The cDNA sequence and deduced amino acid sequence showed that the gene cloned was ~99% homologous with the human ABCA5 protein.

Oligonucleotide Synthesis:

The oligonucleotides were synthesized and purified by HPLC (Biosource International Inc., CA). The gene product of ABCA5 was analyzed with SDS-PAGE and EMSA assays.

RT-PCR Analysis:

RNA was isolated from different patient tissues according to methods described elsewhere herein and subsequently prepared for RT-PCR. RT-PCR was carried out with primers for the ABCA5 genes described elsewhere herein. cDNA (~100 bp) was extracted from the gels for sequencing. Blast analysis and comparisons on Genbank were carried out for each RNA specimen.

Real Time qRT-PCR:

Total RNA was isolated from tissues following a protocol described by 'RNAgents Total RNA Isolation System' (Promega). Custom-made primers were obtained from Integrated DNA Technologies (Coraville, Iowa). Brilliant SYBR Green QPCR was used to perform quantitative PCR amplification for ABCA5 and GAPDH specific regions.

ABCA5 gene was amplified using the following primers:

```
Forward:
                                        (SEQ ID NO:4)
5'-3': GGCTGCTATTCTGACCACTCACTATA;

Reverse:
                                        (SEQ ID NO:5)
5'-3': TTAACTGCCCAGACACCATGAT.
```

GAPDH was amplified using:

```
Forward:
                                        (SEQ ID NO:6)
(305) 5'-TGTTACCAACTGGGACGACA (324)
and Reverse:
                                        (SEQ ID NO:7)
(858) 5'-AAGGAAGGCTGGAAAAAGAGC (837).
```

Western Blot Analysis.

Rabbit polyclonal antibodies were raised against an N-terminal peptide, termed P1: 5'-MSTAIREVGVWRQTRTLLLKNY-3'(i.e. +1 to +22) (SEQ ID NO:8); and a C-terminal peptide, term P2: 5'-FS-GLFSALDSHSNLGVISYGVS-3' (i.e. +854 to +876) (SEQ ID NO:9) unique to the ABCA5 protein. The antibodies were partially purified utilizing a Protein A column. Whole cell lysates were prepared and subjected to Western blot analysis as described previously. Blots were probed with rabbit polyclonal anti-ABCA5 (dilution 1:2,000). A secondary horseradish peroxidase-conjugated IgG anti-rabbit antibody (Pierce, Rockford, Ill.) was applied for 1 h (dilution 1:5000), followed by SuperSignal West Pico Chemiluminescent Substrate detection (Pierce, Rockford, Ill.) and exposure on Chemidoc XRS 5 (BioRad, Richmond, Calif.) to visualize immunoreactive bands.

Immunolabeling:

To determine the subcellular localization of ABCA5, CD44 and ABCG2 proteins, whole mount prostate sections were incubated for 45 min at 37° C. with the polyclonal rabbit anti-ABCA5, CD44 (AbCAM Inc., Cambridge, UK) or ABCG2 (Chemicon Inc., Temecula, Calif.) antibodies. Unbound antibodies were removed by rinsing in PBS, followed by incubation for 45 min at 37° C. with HRP-conjugated anti-rabbit antibody as a secondary antibody (Jackson Immunoresearch Laboratories, West Grove, Pa.) according to methods described elsewhere herein.

ELISA:

ELISA assays were carried out utilizing a rabbit polyclonal antibodies raised against an N-terminal peptide of the ABCA5 proteins. ELISAs were according to Antibody Capture Assay technique and methods described by the Antibodies: A Laboratory Manual. All protein measurements were according to methods of Bradford. Consent was obtained from each of the patients in accordance with HIPPA regulations.

A highly sensitive and consistent screening assay for identification of duplexed DNA sequence(s) which bind picogram levels of protein in crude protein extracts from tissue or urine. Using this technique, ~4096 sequence combinations were screened for the identification of a specific 8 mer sequence (i.e. TCCAGCGA, (SEQ ID NO:3)) that appears to bind a single protein present in crude protein extracts from three different specimens of prostate tissue with biopsy-confirmed HGPIN (FIG. 3, lanes 5-7). The band shift apparent by EMSA was not observed in protein extracts from stroma, BPH or PCA tissue derived from the same prostates. Attempts to increase the amount of $^{32}$P-radiolabeled probe (i.e. to 150,000 dpm) or the amount of crude protein extract (i.e. to 20 μg) did not produce a signal in the PCA, BPH or stroma preparations, indicating the protein might be uniquely over expressed by HGPIN. Changes in the base sequence of the probe eliminated binding to the PIN-protein (data not shown). Similar studies with urine (~10 μg protein) from patients with biopsy positive HGPIN and no indication of cancer showed a similar band shift (FIG. 1b, lanes 1-3 and 6). The band shift was not detected in the urine of patients with BPH or PCA (FIG. 1b, lanes 4-5). However, a faint band shift was observed with the urine of patients with biopsy results showing HGPIN concurrent with PCA (FIG. 1b, lane 6). In the above assays, cold competition experiments with excess unlabeled DNA probe (20-50 ng) completely blocked the band shift observed with HGPIN tissue extracts and HGPIN urine, but a random DNA sequence failed to block binding to the DNA.

Example 1

Cloning of ABCA5

The applicants have utilized a 'Monte Carlo'-like DNA binding assay (International Application No. PCT/US03/14098 of Stearns et al.) to screen for novel duplexed DNA binding sequences which bind protein(s) over expressed in PIN. The 8 bp DNA sequence identified binds ABCA5 protein in crude protein extracts in vitro in electrophoretic mobility shift assays (EMSAs). The Applicants have further determined that there is overexpression of the ABCA5 protein in human PIN tissue and in urine of patients with PIN. The ABCA5 gene has been cloned by in situ hybridization of the 8 bp DNA with ABCA5 protein expressed by phagemid clones in a cDNA expression library. Sequencing revealed that the ABCA5 gene was ostensibly identical to a published cDNA sequence for human ABCA5 gene (Gene Bank Accession Nos. AJ512612; AK122145).

Figure 5:
FIG. 5 is an x-ray film image of a gel from an EMSA showing binding of the $^{32}$P-ATP radiolabeled probe (SEQ ID NO:3) to the ABCA5 protein in crude protein extracts from PIN tissue (lane 1), and to recombinant ABCA5 protein in crude protein extracts of three different lambda phage clones, termed λPIN-1 (lane 2), λPIN-2 (lane 3), and λPIN-3 (lane 4).
Figure 6:
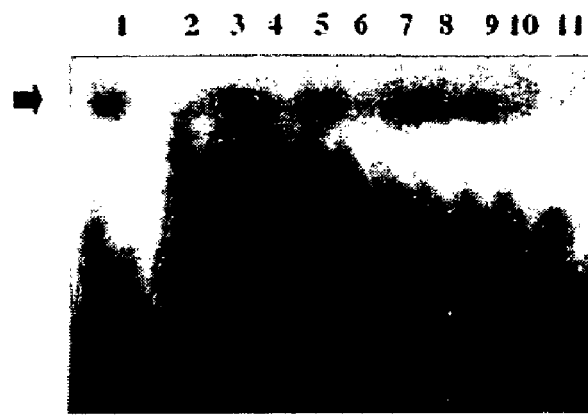
FIG. 6 is an image of a gel blot illustrating protein (1 mg) from urine of patients diagnosed with: HGPIN (lanes 1, 3, 5, 7 and 9), BPH (lanes 2 and 4), and PCA (lanes 6, 8, 10, 11).

Cloning of the ABCA5 gene was carried out utilizing a phage-ZAP Expression vector (Stratagene) according to methods modified from Singh et al., as described elsewhere herein. Three positive clones were identified by autoradiography. These clones were expanded and an EMSA was carried out with crude protein extracts from each clone alongside an extract from prostate tissue with HGPIN. As shown in FIG. 5, each of the three clones showed a single band shift in the EMSA (FIG. 5, lanes 2-4). The band shift was identical to that detected with the HGPIN protein extract (FIG. 5, lane 1). Sequencing of the gene (3321 bases) and blast analysis revealed that it was >98% homologous to the ABCA5 gene. The deduced amino acid sequence (968 a.a.) was also >98% homologous to the ABCA5 protein. EMSA with the $^{32}$P-labeled TCCAGCGA (SEQ ID NO:3) probe subsequently confirmed that ABCA5 was preferentially over expressed in prostate tissue with HGPIN (n=11) when compared with normal (n=12), BPH (n=12) or PCA (n=12) tissue. FIG. 6 further illustrates that ABCA5 was over expressed in urine of patients with HGPIN (FIG. 6, lanes 1, 3, 5, 7 and 9), but was not found in the urine of patients diagnosed with BPH (FIG. 6, lanes 2 and 4) or PCA (FIG. 6, lanes 6, 8, 10 and 11). Again, the specific affinity of the $^{32}$P-labeled TCCAGCGA (SEQ ID NO:3) probe for the urine ABCA5 protein was demonstrated by 'super-shift' assays. EMSAs with increased amounts of the ABCA5 antibody produced protein-antibody complexes near the tops of the gels, indicating the $^{32}$P-labeled TCCAGCGA (SEQ ID NO:3) probe specifically binds the ABCA5 protein. In addition, 'cold competition' experiments with the TCCAGCGA (SEQ ID NO:3) probe (i.e. 20-50 ng) eliminated the 'band-shift' normally observed. Cold competition assays where 1 base was changed or with a random oligonucleotide sequence failed to block the band shift observed with urine protein (5 µg total protein).

Example 2

Western Blots

Figure 9:
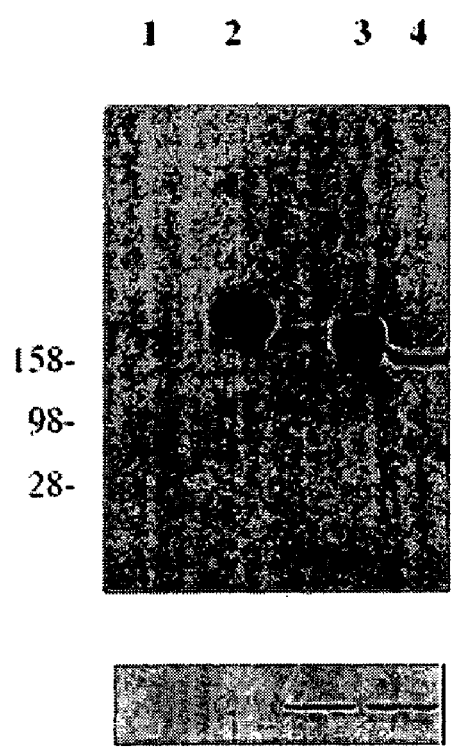
FIG. 9 is an image of a Western-blot with rabbit polyclonal antibodies recognizing the n-terminal domain P1 peptide. Samples include: (lane 1) bacterial plasmid only; (lanes 2, 3) purified ABCA5 protein; and (lane 4) crude urine protein (5 µg). Lower band: β-actin.

Western blots illustrated that both rabbit polyclonal antibodies specifically recognized the 160 KDa recombinant ABCA5 protein (968 a.a.) and a similar size protein present in the urine of a patient with HGPIN (FIG. 9). The antibodies were raised against peptide domains unique to the ABCA5 protein and did not recognize other multi-drug resistant genes (i.e. ABCG2, ABCB1, mdr-1) or other proteins present in recombinant phagmid extracts or whole cell extracts of prostate cells.

Example 3

Immunolabeling Studies

Figure 10:
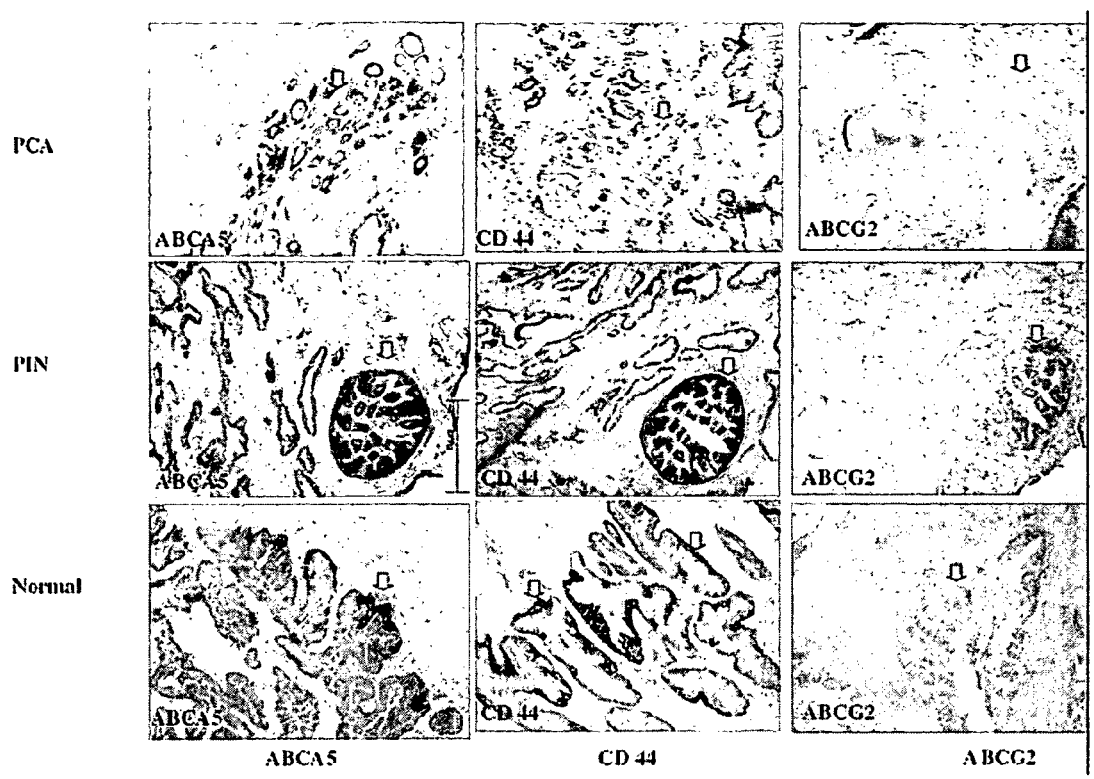
FIG. 10 is a series of images depicting the immunolabeling of human prostate cancer (PCA), prostatic intraepithelial neoplasia (HGPIN), and normal glands with rabbit polyclonal antibodies specific for ABCA5, and antibodies specific for CD 44 and ABCG2. Shows that ABCA5 was selectively expressed in intermediate basal cells of normal glands (arrow) and was faintly expressed in an irregular fashion in PCA (arrow). ABCA5 was over expressed in HGPIN (arrow). CD44 was highly expressed in normal basal cells and HGPIN and PCA (arrow). ABCG2, an (analogue of ABCA5) was not expressed in Benign, HGPIN or PCA (arrow).

Immunolabeling of human prostate glands (n=10 whole mount prostates) confirmed that the ABCA5 protein was selectively expressed in glands with HGPIN lesions and not expressed in BPH or faintly expressed in normal glands and PCA (FIG. 10). Note that in normal glands, the occasional foci of intermediate basal cells (arrow) were strongly labeled with the ABCA5 antibodies, suggesting these cells might be the origin of HGPIN (FIG. 10). Note also that CD44 antibodies labeled the vast majority of the basal cells plus the intermediate basal cells. CD44 antibodies faintly labeled the luminal epithelial cells of PCA. In comparison, ABCG2, a homologue of ABCA5, failed to label the basal cells or intermediate basal cells or HGPIN and PCA cells in any of the specimens examined (n=10).

Example 4

PCR and qRT-PCR Assays

PCR analysis to amplify mRNA isolated from different types of prostate tissue (n=5) (i.e., normal, BPH, HGPIN, PCA) combined with sequencing of the 100b fragments revealed that ABCA5 was highly expressed in HGPIN whereas it was only faintly expressed in tissue specimens of prostate carcinoma. qRT-PCR and comparisons of the relative levels of expression of ABCA5 in different tissues clearly showed that the ABCA5 gene was over expressed in HGPIN, but not expressed in BPH, PCA, normal prostate or prostate stroma (FIG. 11). Likewise, ABCA5 was not expressed in bladder, kidney cancer and lung cancer (FIG. 11) or in PCA cells shed in the urine. However, ABCA5 was over expressed in seminal vesicle, kidney, liver and testis (but not testis cancer)(FIG. 11), in agreement with a previous report of Langmann et al.

Example 5

ELISAs

Utilizing the P1 polyclonal antibodies, an ELISA was developed using purified recombinant ABCA5 protein. The standard curve (FIG. 12) showed that the limit of detection of ABCA5 was ~1 ng/0.1 ml. A linear increase in absorbance was observed for increased amounts of ABCA5 ranging from 1 to 23 ng/0.1 ml with a correlation coefficient of 0.54. Note that an absorbance (A 450 nm) of 0.2 nm corresponded to ~2.0 ng/0.1 ml ABCA5 P1 peptide. The addition of increased amounts of P1 peptide to the negative urine, yielded a standard curve identical to that observed with PBS. In FIG. 13a, the levels of ABCA5 protein were assayed in urine specimens (from BioReclamation Inc., Willmington, Del.) collected from patients with PSA <1.5 ng/ml (n=30) compared with patients with serum PSA >10 ng/ml (n=30), without the benefit of biopsy. The data showed that >97% of the patients with high PSA levels also had elevated ABCA5 levels in their urine (i.e. >25 ng/ml). In comparison, >90% of the patients with low PSA levels (<1.5 ng/ml) also had low levels of ABCA5 in their urine (i.e. <25 ng/ml) (FIG. 13a). One interpretation of this result is that urine from patients with levels of PSA <1.5 ng/mL, considered to be putatively normal patients (i.e., no PCA or HGPIN), also exhibited low levels of ABCA5. However, patients with elevated levels of PSA who would be considered to have carcinoma of the prostate were found to have elevated ABCA5 levels, which is consistent with the concurrence of HGPIN and PCa in the prostates of these patients. The PSA values for the HGPIN patients ranged from 0.3 to 42.8 ng/ml, with the majority of the patients exhibiting PSA values >4 ng/ml. There was no correlation of the PSA values with the incidence of HGPIN or the ABCA5 levels in urine ($R^2$=0.998). FIG. 13b shows data from 'blinded study' of patient urine (obtained from GTx, Inc.) (n=195 total). Patients had been previously diagnosed with benign disease and biopsy negative for HGPIN, n=79); PCA (biopsy positive for PCA, n=9) (but some of the samples were also biopsy positive for HGPIN); and HGPIN only (biopsy positive for high grade HGPIN, n=107). The data shows the amounts of ABCA5 (ng/ml)(i.e. normalized per ml in the urine samples). The sensitivity was >98.1% and the specificity was >86% at a cut off of 25 ng/ml. That is, the levels of ABCA5 were above the cut-off of 25 ng/ml in the biopsy positive HGPIN patients, and below 25 ng/ml in the patients biopsy negative for HGPIN. The range of detection was from ~25 ng/ml to 220 ng/ml in the HGPIN patients. The assay conditions were identical to the methods described for the standard curve (FIG. 12).

Example 6

Reproducibility and Precision

Repeat assays with 10 different specimens positive for HGPIN and 10 BPH specimens (i.e. negative for HGPIN) have shown that all the HGPIN were positive for ABCA5 and all the BPH were negative for ABCA5. More importantly, the measurements from repeat assays were consistent (S.E. <0.5 ng/0.1 ml and <0.1 ng/0.1 ml, respectively).

Example 7

Antigen Characteristics

Preliminary studies have been carried out to evaluate antigen stability and the precision of the assay for ABCA5 in the urine. The data from repeated measurements of urine specimens showed that ABCA5 is a very stable protein and that the signal is not diminished >0.5 ng/0.1 ml if urine is kept at 4° C. for 1 week or frozen for 1 year or and frozen and thawed 3 times. Dilution of the urine with PBS (1:1) slightly diminished the signal by ~10%. Repeated assays on the sample indicated that ~70% of the ABCA5 protein was captured in the first assay and that <5% remained after 2 assays. Finally, the dilution of positive HGPIN urine with negative urine specimens from PCA or BPH patients did not eradicate the signal, but simply reduced the level of ABCA5 in accordance with dilution effects of the added urine, indicating these urines did not contain an interference factor.

Discussion of Experimental Examples

Development of a diagnostic marker for HGPIN is important as several major studies have shown that HGPIN is a precursor of prostate cancer. The overall prognosis is that ~35% of the patients diagnosed with HGPIN get prostate cancer within 1 year of diagnosis, and ~50% of these patients get cancer after 2 years. The ABCA5 protein and ABCA5 gene have been identified herein as being over expressed in HGPIN tissue. The ABCA5 protein was not found or was faintly expressed in PCA, BPH, and stroma tissue of the prostate, by comparison. Interestingly, immunolabeling indicated that ABCA5 was uniquely expressed in histologically defined intermediate basal cell foci found in normal glands, and was over expressed in all the cells of HGPIN glands. These results demonstrate that the ABCA5 positive intermediate basal cells may constitute a highly proliferative cell type which is the precursor of HGPIN. The ABCA5 protein has also been identified herein as a urine biomarker for HGPIN. While not wishing to be bound by any one theory, ABCA5 may serve as a biomarker due to a direct result of the proliferation and sloughing of HGPIN cells in the lumen of glands and subsequently shedding in the urine. The ABCA5 protein was found in urine at levels ranging from 25-250 ng/ml, a direct result of the lyses of HGPIN cells in the hypotonic urine.

Additionally, in a 'blinded study' of >195 patients (of which 107 patients were found biopsy-positive for HGPIN) described herein, the ABCA5 protein was present in the urine at elevated levels compared to the biopsy negative patients (n=79). In the latter population, we found that the ABCA5 protein was either not present in the urine or was present at very low levels (i.e. <25 ng/ml). The overall sensitivity and specificity of the ABCA5 marker was >98.1% and 86%, respectively, with a limit of detection of 25 ng/ml at an absorbance of A450 nm.

In sum, by identifying a marker that is specific for HGPIN, not merely for the prostate, the assay for the ABCA5 protein offers a means to improve on the early detection of premalignant prostate cancer (i.e. HGPIN), thereby reducing biopsies when used as an adjunct to current methods. Moreover, a urine assay such as ABCA5 is convenient and noninvasive, since a needle puncture is not required to collect urine, and therefore can readily be added to existing diagnostic tools.

It is important to emphasize that although the ABCA5 protein was over-expressed in all the cells of the HGPIN glands, ABCA5 was not merely expressed by the HGPIN glands. That is, the ABCA5 protein was over expressed by a unique foci of cells, termed intermediate basal cells, in normal glands. It was not expressed by other basal cells or luminal epithelial cells of normal glands, however. In addition, ABCA5 was faintly expressed by the luminal epithelial cells of PCA (FIG. 10), indicating the HGPIN cells which express ABCA5 may give rise to PCA. This means that although the urine levels of ABCA5 are significantly elevated in patients with HGPIN, low levels of ABCA5 may be found in the urine of patients with normal conditions or PCA. In this regard, it was found that some of the PCA patients had elevated HGPIN urine levels (see FIG. 13b), and further biopsy is required to establish the HGPIN status of such patients, as HGPIN is commonly present in the prostates of patients with PCA (and is often missed by biopsy). Additional studies can also be used to compare urine levels of ABCA5 in a patient's biopsy positive for PCA and PCA+HGPIN versus HGPIN patients to determine whether the ABCA5 test can discriminate between these 2 patent populations. In addition, comparison of ABCA5 urine levels to serum PSA and DRE data plus patient age may help better identify the stage patients with premalignant and early stage cancer, for example.

The cloning protocol used to identify the ABCA5 gene was based on a procedure previously developed to isolate a diagnostic marker for prostate cancer, termed PCADM-1 (24). In these studies a novel duplexed probe was identified which binds a leucine zipper domain of a mutant S2 ribosomal protein. In the present patent application, the duplexed TCCAGCGA (SEQ ID NO:3) probe, which presumably binds a specific consensus domain of the ABCA5 protein, was identified.

The ATP-binding cassette (ABC) transporter superfamily is a large gene family comprising at least 48 genes and encodes a functionally diverse group of multispan membrane proteins involved in energy-dependent transport of a wide variety of substrates across membranes. Some multiple drug resistance phenotypes in tumor cells have been associated with the gene encoding the MDR (multi-drug resistance) protein, which also has an ABC transporter structure. Several ABC proteins in the human system are responsible for drug exclusion in compound-treated tumor cells, providing cellular mechanisms for the development of multidrug resistance. One group contains five genes (ABCA5, ABCA6, ABCA8, ABCA9, and ABCA10) arranged in a cluster on chromosome 17q24. Two members of this subfamily, the ABCA 1 and ABCA4 (ABCR) proteins, have been studied extensively. The ABCA1 protein is involved in disorders of cholesterol transport and high-density lipoproteins (HDL) biosynthesis (see below). The ABCA4 protein transports vitamin A derivatives in the outer segments of photoreceptor cells and therefore performs a crucial step in the visual cycle. Human ABCA5 and rat Abca5 (rAbca5) represent recently identified subfamily members. Quantitative RT-PCR showed that a ABCA5 splice variant was expressed in numerous tissues (including testis, brain and lung). The substrate spectrum remains to be defined and its normal function in different cell types and tissues is unknown. It has been shown to co-localized with a marker protein for the Golgi apparatus in Leydig cells, and it has been suggested it may play a role in intracellular sterol/steroid trafficking. Whether it also plays a role in drug resistance is not known.

Because ABC genes are prone to be involved in cancer progression and drug resistance, ABCA5 may confer drug resistance on the HGPIN cells. Thus, based on the disclosure set forth herein, ABCA5 may be a promising target molecule for development of a therapeutic for the treatment of HGPIN, and possibly reduce HGPIN progression to PCA.

Since HGPIN has been shown to be more predictive of PCA in older patients and those with a serum PSA of >4 ng/ml, a therapeutic approach for treating HGPIN may be of tremendous benefit to these individuals at high risk for prostate cancer (i.e. older men, brothers of siblings with PCA, and Afro-Americans). A variety of treatments are currently being developed for precancerous lesions of PCA. HGPIN has been identified as a target of several chemopreventive agents including green tea polyphenols, soy isoflavones, SERMS (i.e. Acapodene), for example. Thus, a non-invasive assay, such as the ABCA5 test, would be of tremendous benefit. This is especially true in light of the ongoing debate in the clinical diagnostic community as to whether HGPIN can be routinely detected and diagnosed by pathologists. Detecting HGPIN by biopsy is extremely difficult and this problem is compounded by the fact that HGPIN lesions tend to be small and scattered throughout the prostate gland. If HGPIN is a precursor to PCA, a specific HGPIN assay would be invaluable not only for early detection of cancer but also for monitoring the progression from HGPIN to PCA. Likewise, the assay (i.e. ABCA5) would be of potential use in monitoring the response to therapies developed to prevent HGPIN from progressing to PCA (i.e. Acapodene or Toremifene citrate).

In an ongoing trial, Toremifene citrate, which is a selective estrogen receptor modulator (SERM) compound that was originally developed as an anti-estrogen and is currently marketed as Fareston® for advanced breast cancer in women. Toremifene has been convincingly shown to prevent HGPIN-like lesions and prevent or delay the onset of prostate tumors in the mouse prostate TRAMP model. In addition, a placebo-controlled Phase IIb clinical trial was conducted by GTx, Inc., for the treatment of HGPIN using prostate cancer on a follow-up biopsy as a primary endpoint. The study included 514 cancer-free patients with affirmed HGPIN. Results showed the risk of prostate cancer incidence was 24.4% in the 20 mg Toremifene treatment group (n=114) compared with 31.2% in the placebo group (n=109), representing a 21.8% (p=0.048) cumulative risk reduction in prostate cancer. The Phase IIb trial was the largest study of the natural history of prostate cancer to date, and included the collection of specimens, both blood and urine, for the purpose of biomarker discovery to improve screening and detection of HGPIN. Based on the promising results of the Phase IIb study, a double-blind, randomized, multi-center, Phase III trial is ongoing with ~1260 patients to confirm the efficacy of toremifene 20 mg/day versus placebo for prevention of invasive prostatic adenocarcinoma in high-risk men. The materials and methods of the present invention can be used to determine whether the ABCA5 protein is a diagnostic marker which can predict HGPIN, and/or predict the failure of HGPIN to progress to PCA in Toremifene treated patients.

PUBLICATIONS AND REFERENCES

Kovi, J., Mostofi, F. K., Heshmat, M. Y., and Enterline, J. P. Large acinar atypical hyperplasia and carcinoma of the prostate. Cancer 61:555-561, 1988.

Quinn, B. D., Cho, K. R., and Epstein, J. I. Relationship of severe dysplasia to Stage A (incidental) adenocarcinoma of the prostate. Cancer 65:2321-2327, 1990.

Brawer, M. K., Bigler, S. A., Sohlberg, O. E., Nagle, R. B., and Lange, P. H. Significance of prostatic intraepithelial neoplasia on prostate needle biopsy. Urology 38:103-107, 1991.

Weinstein, M. H., Epstein, J. I. Significance of high grade prostatic intraepithelial neoplasia on needle biopsy. Human Pathol. 24:624-629, 1993.

Sakr, W. A., Grignon, .D J, Crissman, J. D., Heilbrun, L. K., Cassin, B. J., Pontes, J. J., and Haas, G. P. High grade prostatic intraepithelial neoplasia (HGPIN) and prostatic adenocarcinoma between the ages of 20-69: an autopsy study of 249 cases. In Vivo 8:439-443, 1994.

Bostwick, D. G, Prostatic Intraepithelial Neoplasia. The most likely precursor of prostate cancer., Cancer 75:1823-1836, 1995(a).

Bostwick, D. G, and Qian, J., Atypical adenomatous hyperplasia of the prostate: Relationship with carcinoma in 217 whole mount radical prostatectomies., Am J Surg Pathol 19:506-518, 1995(b).

Davidson, D., Bostwick, D. G, Qian J., Wollan, P. C, Oesterling J. E., Rudders, R. A, Siroky, M., and Stilmant, M, Prostatic intraepithelial neoplasia is a risk factor for adenocarcinoma predictive accuracy in needle biopsies., J. Urol. 154:1295-1299, 1995.

Arakawa A., Song, S., Scardino P. T., and Wheeler T. M., High grade prostatic intraepithelial neoplasia in prostates removed following irradiation failure in the treatment of prostatic carcinoma. Pathol. Res. Pract. 191:868-872, 1995.

Haggman, M. J., Macoska, J. A., Wojno, K. J., Oesterling, J. E. The relationship between prostatic intraepithelial neoplasia and prostate cancer: critical issues. J. Urol. 158:12-22, 1997.

Qian, J., Wollan, P., and Bostwick, D. G. The extent and multicentricity of high-grade prostatic intraepithelial neoplasia in clinically localized prostatic adenocarcinoma., Hum. Pathol. 28:143-148, 1997.

Sakr, W. A. Prostatic intraepithelial neoplasia: A marker for high-risk groups and a potential target for chemoprevention, Eur. Urol. 35:474-478, 1999.

Orozco, R., O'Dowd, G., Kunnel, B., Miller, M. C., Veltri, R. W. Observations on pathology trends in 62,537 prostate biopsies obtained from urology private practices in the United States., Urology 51:186-195, 1998.

Gokden, N., Roehl, K. A, Catalona, W. J., and Humphrey, P. A. High-grade prostatic intraepithelial neoplasia in needle biopsy as risk factor for detection of adenocarcinoma: current level of risk in screening population. Am J Surg Pathol. 2004 May; 28(5):629-33

Bishara, T., Ramnani, D. M., and Epstein, J. I. High-grade prostatic intraepithelial neoplasia on needle biopsy: risk of cancer on repeat biopsy related to number of involved cores and morphologic pattern. Am J Surg Pathol., 28:629-33, 2004.

Bostwick, D. G, Brawer M K: Prostatic intraepithelial neoplasia. and early invasion in prostate cancer. Cancer 59:788-794, 1987.

Bostwick, D. G. High grade prostatic intraepithelial neoplasia: the most likely precursor of prostate cancer. Cancer, 75: 1823-1836, 1995.

Singh, H., Lebowitz, J. H., Baldwin, A. S., and Sharp, P. A. Molecular cloning of an enhancer binding protein: isolation by screening of an expression library with a recognition site DNA. Cell 52:415-423, 1988.

Ohkia, A., Hu, Y., Wang, M., Garcia, F. U. and Stearns, M. E. Evidence for a Prostate Cancer Associated Diagnostic Marker-1, PCADM-1: Immunohistochemistry and In situ hybridization studies. Clin. Can. Res. 10; 2452-2458, 2004.

Frangioni, J. V., and Neel, B. G. Solubilization and purification of enzymatically active glutathione S-transferase (pGEX) fusion proteins. Analytical Biochemistry 210, 179-187, 1993.

Sambrook, J., Fritsch, E. D., and Maniatis, T. Molecular cloning. A laboratory manual. 2nd edition. Cold Spring Harbor Laboratory Press. Vol 1: pp 2.82-2.108, 1989.

Langmann, T., Mauerer, R., Zahn, A., Moehle, C., Probst, M., Stremmel, W., and Schmitz, G. Real-Time Reverse Transcription-PCR Expression Profiling of the Complete Human ATP-Binding Cassette Transporter Superfamily in Various Tissues. Clinical Chemistry 49, 230-238, 2003.

Towbin, H., Staehelin, T., and Gordon, J. Electrophoretic transfer of proteins from polyacrylamide gels to nitrocellulose sheets; procedures and some applications. Proc. Natl. Acad. Sci. U.S.A. 76:4350-4354, 1979.

Stearns, M. E., and Wang, M. Immunoassays of the Metalloproteinase (MMP-2) and Tissue Inhibitor of Metalloproteinase (TIMP-1, 2) Levels in Non-Invasive and Metastatic PC-3 Clones. Effects of Taxol. Oncol. Res. 6:195-201, 1994.

Ed Harlow., David Lane. Antibodies A Laboratory Manual. Cold Spring Harbor Laboratory. P.563-566, 1988.

Bradford, M. M. A rapid and sensitive method for the quantitation of microgram quantities of protein utilizing the principles of protein-dye binding. Anal. Biochem., 72:248-254, 1976.

A. Scholler, Freibauer, C; Wang, Min; Hu, Youji; and Stearns, M. E. Austrian AUA Mttg, 36a, 2006.

Dean, M., Hamon, Y., Chimini, G. The human ATP-binding cassette (ABC) transporter superfamily. J Lipid Res 42:1007-17, 2001.

Litman T., Druley, T. E., Stein, W. D., Bates, S. E. From MDR to MXR: new understanding of multidrug resistance systems, their properties and clinical significance. Cell Mol Life Sci. 58:931-59, 2001.

Schmitz, G., and Drobnik, W. ATP-binding cassette transporters in macrophages: promising drug targets for treatment of cardiovascular disease. Curr Opin Investig Drugs 3:853-859, 2002.

Dean, M., Rzhetsky, A., and Allikmets, R. The Human ATP-Binding Cassette (ABC) Transporter Superfamily. Genome Res. 11, 1156-1166, 2001.

Petry, F, Ritz, V, Meineke, C, Middel, P, Kietzmann, T, Schmitz-Salue, C, Hirsch-Ernst, K I. Subcellular localization of rAbca5, a rat ATP-binding cassette transporter expressed in Leydig cells, and characterization of its splice variant apparently encoding a half transporter. Biochem J., 393:79-87, 2006.

Petry, F., A. Kotthaus, and K. I. Hirsch-Ernst. Cloning of human and rat ABCA5/Abca5 and detection of a human splice variant. Biochem. Biophys. Res. Commun. 300:343-350. 2003.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The disclosures of each and every patent, patent application, and publication cited herein are hereby incorporated herein by reference in their entirety.

What is claimed is:

1. A method of diagnosing high grade prostatic intraepithelial neoplasia in a human suspected of having high grade prostatic intraepithelial neoplasia, said method comprising:
   a. obtaining a biological sample from said human;
   b. determining the level of ATP-binding cassette transporter 5 polypeptide in said biological sample;
   c. comparing the level of ATP-binding cassette transporter 5 polypeptide in said biological sample with the level of ATP-binding cassette transporter 5 polypeptide in a biological sample obtained from a like human not afflicted with high grade prostatic intraepithelial neoplasia;
   wherein said biological sample is selected from the group consisting of a urine sample and a prostate tissue sample;
   wherein said ATP-binding cassette transporter 5 polypeptide comprises the polypeptide of SEQ ID NO: 2; and
   wherein when a higher level of ATP-binding cassette transporter 5 polypeptide is determined in said biological sample from said human as compared with the level of ATP-binding cassette transporter 5 polypeptide in said biological sample from said like human, the human is diagnosed with high grade prostatic intraepithelial neoplasia.

2. The method of claim 1, wherein said determining presence or level of ATP-binding cassette transporter 5 polypeptide in said biological sample is conducted by an assay selected from the group consisting of a DNA binding EMSA assay, ELISA, and Western blot.

3. The method of claim 2, wherein said assay is performed with an antibody which specifically binds ATP-binding cassette transporter 5 polypeptide.

4. A method of diagnosing high grade prostatic intraepithelial neoplasia in a human suspected of having high grade prostatic intraepithelial neoplasia, said method comprising:
   a. obtaining a biological sample from said human;
   b. determining the level of ATP-binding cassette transporter 5 mRNA in said biological sample;
   c. comparing the level of ATP-binding cassette transporter 5 mRNA in said biological sample with the level of ATP-binding cassette transporter 5 mRNA in a biological sample obtained from a like human not afflicted with high grade prostatic intraepithelial neoplasia;
   wherein said biological sample is selected from the group consisting of a urine sample and a prostate tissue sample;
   wherein said ATP-binding cassette transporter 5 mRNA comprises a mRNA complementary to the polynucleotide of SEQ ID NO: 1; and
   wherein when a higher level of ATP-binding cassette transporter 5 mRNA is determined in said biological sample from said human as compared with the level of ATP-binding cassette transporter 5 mRNA in said biological sample from said like human, the human is diagnosed with high grade prostatic intraepithelial neoplasia.

5. The method of claim 4, wherein said determining presence or level of ATP-binding cassette transporter 5 mRNA in said biological sample is conducted by an assay selected from the group consisting of a RT-PCR, in situ hybridization and Northern blot.

* * * * *

UNITED STATES PATENT AND TRADEMARK OFFICE
CERTIFICATE OF CORRECTION

| | | |
|---|---|---|
| PATENT NO. | : 7,666,584 B2 | Page 1 of 1 |
| APPLICATION NO. | : 11/515475 | |
| DATED | : February 23, 2010 | |
| INVENTOR(S) | : Stearns | |

It is certified that error appears in the above-identified patent and that said Letters Patent is hereby corrected as shown below:

Col. 1 line 21, change "CA76639" to "CA076639"

Line 22, change "may therefore have certain rights" to "therefore has rights"

Signed and Sealed this
Twentieth Day of September, 2011

David J. Kappos
*Director of the United States Patent and Trademark Office*